US012746020B2

(12) United States Patent
Hakala et al.

(10) Patent No.: US 12,746,020 B2
(45) **Date of Patent: *Sep. 29, 2026**

(54) SHOCKWAVE CATHETER SYSTEM WITH ENERGY CONTROL

(71) Applicant: Shockwave Medical, Inc., Santa Clara, CA (US)

(72) Inventors: Doug Hakala, Woodinville, WA (US); John M. Adams, Snohomish, WA (US); Randy Holmberg, Bothell, WA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 124 days.

This patent is subject to a terminal disclaimer.

(21) Appl. No.: 18/814,977

(22) Filed: Aug. 26, 2024

(65) Prior Publication Data

US 2025/0057554 A1 Feb. 20, 2025

Related U.S. Application Data

(63) Continuation of application No. 18/105,584, filed on Feb. 3, 2023, now Pat. No. 12,096,950, which is a (Continued)

(51) Int. Cl.

*A61B 17/22* (2006.01)
*A61B 17/225* (2006.01)
*A61B 17/00* (2006.01)

(52) U.S. Cl.

CPC ...... *A61B 17/22022* (2013.01); *A61B 17/225* (2013.01); *A61B 2017/00039* (2013.01); (Continued)

(58) Field of Classification Search

CPC ... A61B 17/22; A61B 17/225; A61B 17/2255; A61B 17/2256; A61B 17/2258; (Continued)

(56) References Cited

U.S. PATENT DOCUMENTS 2,916,647 A 12/1959 George
3,412,288 A 11/1968 Ostrander
(Continued)

FOREIGN PATENT DOCUMENTS

AU 2009313507 B2 11/2014
AU 2013284490 B2 5/2018
(Continued)

OTHER PUBLICATIONS

"FDA Clears Lithoplasty Balloon That Shatters Calcified Lesions With Ultrasound", Diagnostic and Interventional Cardiology, Available Online at <https://www.dicardiology.com/product/fda-clearslithoplasty-balloon-shatters-calcified-lesions-ultrasound>, Sep. 16, 2016, pp. 1-5.

(Continued)

*Primary Examiner* — Tuan V Nguyen

(74) *Attorney, Agent, or Firm* — Morrison & Foerster LLP

(57) ABSTRACT

A system that breaks calcium in a liquid includes a catheter including first and second electrodes arranged to receive there-across a high electrical voltage at an initial low current. The high electrical voltage causes an electrical arc to form across the electrodes creating a gas bubble within the liquid, a high current to flow through the electrodes, and a mechanical shock wave. A power source provides the electrodes with the high electrical voltage at the initial current and terminates the high electrical voltage in response to the high current flow through the electrodes.

19 Claims, 5 Drawing Sheets

Related U.S. Application Data continuation of application No. 17/198,001, filed on Mar. 10, 2021, now Pat. No. 11,596,424, which is a continuation of application No. 16/222,679, filed on Dec. 17, 2018, now Pat. No. 10,973,538, which is a continuation of application No. 15/065,607, filed on Mar. 9, 2016, now Pat. No. 10,159,505, which is a continuation of application No. 13/615,107, filed on Sep. 13, 2012, now Pat. No. 9,333,000.

(52) U.S. Cl.
CPC ............... *A61B 2017/22025* (2013.01); *A61B 2017/22065* (2013.01)

(58) Field of Classification Search
CPC ............ A61B 17/2202; A61B 17/2204; A61B 17/22012; A61B 17/22022; A61B 17/22029; A61B 2017/00039; A61B 2017/22025; A61B 2017/22065
See application file for complete search history.

(56) References Cited

U.S. PATENT DOCUMENTS 3,413,976 A 12/1968 Roze
3,524,101 A 8/1970 Barbini
3,583,766 A 6/1971 Padberg
3,785,382 A 1/1974 Schmidt-Kloiber et al.
3,902,499 A 9/1975 Shene
3,942,531 A 3/1976 Hoff et al.
4,027,674 A 6/1977 Tessler et al.
4,030,505 A 6/1977 Tessler
4,445,509 A 5/1984 Auth
4,662,126 A 5/1987 Malcolm
4,662,375 A 5/1987 Hepp et al.
4,671,254 A 6/1987 Fair
4,685,458 A 8/1987 Leckrone
4,741,405 A 5/1988 Moeny et al.
4,809,682 A 3/1989 Forssmann et al.
4,813,934 A 3/1989 Engelson et al.
4,878,495 A 11/1989 Grayzel et al.
4,890,603 A 1/1990 Filler
4,900,303 A 2/1990 Lemelson
4,990,134 A 2/1991 Auth
4,994,032 A 2/1991 Sugiyama et al.
5,009,232 A 4/1991 Hassler et al.
5,046,503 A 9/1991 Schneiderman
5,057,103 A 10/1991 Davis
5,057,106 A 10/1991 Kasevich et al.
5,061,240 A 10/1991 Cherian
5,078,717 A 1/1992 Parins et al.
5,102,402 A 4/1992 Dror et al.
5,103,804 A 4/1992 Abele et al.
5,116,227 A 5/1992 Levy
5,152,767 A 10/1992 Sypal et al.
5,152,768 A 10/1992 Bhatta
5,154,722 A 10/1992 Filip et al.
5,176,675 A 1/1993 Watson et al.
5,195,508 A 3/1993 Muller et al.
5,245,988 A 9/1993 Einars et al.
5,246,447 A 9/1993 Rosen et al.
5,254,121 A 10/1993 Manevitz et al.
5,281,231 A 1/1994 Rosen et al.
5,295,958 A 3/1994 Shturman
5,304,134 A 4/1994 Kraus et al.
5,321,715 A 6/1994 Trost
5,324,255 A 6/1994 Passafaro et al.
5,336,234 A 8/1994 Vigil et al.
5,362,309 A 11/1994 Carter
5,364,393 A 11/1994 Auth et al.
5,368,591 A 11/1994 Lennox et al.
5,395,335 A 3/1995 Jang
5,417,208 A 5/1995 Winkler
5,425,735 A 6/1995 Rosen et al.
5,454,809 A 10/1995 Janssen
5,472,406 A 12/1995 de la Torre et al.
5,582,578 A 12/1996 Zhong et al.
5,584,843 A 12/1996 Wulfman et al.
5,603,731 A 2/1997 Whitney
5,609,606 A 3/1997 O'Boyle
5,662,590 A 9/1997 de la Torre et al.
5,709,676 A 1/1998 Alt
5,846,218 A 12/1998 Brisken et al.
5,891,089 A 4/1999 Katz et al.
5,893,840 A 4/1999 Hull et al.
5,931,805 A 8/1999 Brisken
6,007,530 A 12/1999 Dornhofer et al.
6,033,371 A 3/2000 Torre et al.
6,056,722 A 5/2000 Jayaraman
6,080,119 A 6/2000 Schwarze et al.
6,083,232 A 7/2000 Cox
6,090,104 A 7/2000 Webster et al.
6,113,560 A 9/2000 Simnacher
6,132,444 A 10/2000 Shturman et al.
6,146,358 A 11/2000 Rowe
6,186,963 B1 2/2001 Schwarze et al.
6,210,408 B1 4/2001 Chandrasekaran et al.
6,215,734 B1 4/2001 Moeny et al.
6,217,531 B1 4/2001 Reitmajer
6,267,747 B1 7/2001 Samson et al.
6,277,138 B1 8/2001 Levinson et al.
6,287,272 B1 9/2001 Brisken et al.
6,352,535 B1 3/2002 Lewis et al.
6,364,894 B1 4/2002 Healy et al.
6,367,203 B1 4/2002 Graham et al.
6,371,971 B1 4/2002 Tsugita et al.
6,398,792 B1 6/2002 O'Connor
6,406,486 B1 6/2002 De La Torre et al.
6,440,124 B1 8/2002 Esch et al.
6,494,890 B1 12/2002 Shturman et al.
6,514,203 B2 2/2003 Bukshpan
6,524,251 B2 2/2003 Rabiner et al.
6,589,253 B1 7/2003 Cornish et al.
6,607,003 B1 8/2003 Wilson
6,638,246 B1 10/2003 Naimark et al.
6,652,547 B2 11/2003 Rabiner et al.
6,666,834 B2 12/2003 Restle et al.
6,689,089 B1 2/2004 Tiedtke et al.
6,736,784 B1 5/2004 Menne et al.
6,740,081 B2 5/2004 Hilal
6,755,821 B1 6/2004 Fry
6,939,320 B2 9/2005 Lennox
6,989,009 B2 1/2006 Lafontaine
7,066,904 B2 6/2006 Rosenthal et al.
7,087,061 B2 8/2006 Chernenko et al.
7,241,295 B2 7/2007 Maguire
7,309,324 B2 12/2007 Hayes et al.
7,389,148 B1 6/2008 Morgan
7,505,812 B1 3/2009 Eggers et al.
7,569,032 B2 8/2009 Naimark et al.
7,850,685 B2 12/2010 Kunis et al.
7,853,332 B2 12/2010 Olsen et al.
7,873,404 B1 1/2011 Patton et al.
7,951,111 B2 5/2011 Drasler et al.
8,162,859 B2 4/2012 Schultheiss et al.
8,177,801 B2 5/2012 Kallok et al.
8,353,923 B2 1/2013 Shturman
8,556,813 B2 10/2013 Cioanta et al.
8,574,247 B2 11/2013 Adams et al.
8,728,091 B2 5/2014 Hakala et al.
8,747,416 B2 6/2014 Hakala et al.
8,888,788 B2 11/2014 Hakala et al.
8,956,371 B2 2/2015 Hawkins et al.
8,956,374 B2 2/2015 Hawkins et al.
9,005,216 B2 4/2015 Hakala et al.
9,011,462 B2 4/2015 Adams et al.
9,011,463 B2 4/2015 Adams et al.
9,044,618 B2 6/2015 Adams et al.
9,044,619 B2 6/2015 Adams et al.
9,072,534 B2 7/2015 Hakala et al.
9,138,249 B2 9/2015 Adams et al.
9,198,825 B2 12/2015 Katragadda et al.
9,333,000 B2 5/2016 Hakala et al.

(56) References Cited

U.S. PATENT DOCUMENTS

| | | | |
|---|---|---|---|
| 9,421,025 | B2 | 8/2016 | Hawkins et al. |
| 9,433,428 | B2 | 9/2016 | Hakala et al. |
| 9,522,012 | B2 | 12/2016 | Adams |
| 9,642,673 | B2 | 5/2017 | Adams et al. |
| 9,993,292 | B2 | 6/2018 | Adams et al. |
| 10,039,561 | B2 | 8/2018 | Adams et al. |
| 10,118,015 | B2 | 11/2018 | De La Rama et al. |
| 10,149,690 | B2 | 12/2018 | Hawkins et al. |
| 10,154,799 | B2 | 12/2018 | Van Der Weide et al. |
| 10,159,505 | B2 | 12/2018 | Hakala et al. |
| 10,206,698 | B2 | 2/2019 | Hakala et al. |
| 10,517,620 | B2 | 12/2019 | Adams |
| 10,517,621 | B1 | 12/2019 | Adams |
| 10,555,744 | B2 | 2/2020 | Nguyen et al. |
| 10,682,178 | B2 | 6/2020 | Adams et al. |
| 10,702,293 | B2 | 7/2020 | Hawkins et al. |
| 10,709,462 | B2 | 7/2020 | Nguyen et al. |
| 10,959,743 | B2 | 3/2021 | Adams et al. |
| 10,973,538 | B2 | 4/2021 | Hakala et al. |
| 11,000,299 | B2 | 5/2021 | Hawkins et al. |
| 11,076,874 | B2 | 8/2021 | Hakala et al. |
| 11,337,713 | B2 | 5/2022 | Nguyen et al. |
| 11,432,834 | B2 | 9/2022 | Hakala et al. |
| 11,534,187 | B2 | 12/2022 | Bonutti |
| 11,596,424 | B2 | 3/2023 | Hakala et al. |
| 11,622,780 | B2 | 4/2023 | Nguyen et al. |
| 11,696,799 | B2 | 7/2023 | Adams et al. |
| 11,771,449 | B2 | 10/2023 | Adams et al. |
| 2001/0044596 | A1 | 11/2001 | Jaafar |
| 2002/0045890 | A1 | 4/2002 | Celliers et al. |
| 2002/0082553 | A1 | 6/2002 | Duchamp |
| 2002/0177889 | A1 | 11/2002 | Brisken et al. |
| 2003/0004434 | A1 | 1/2003 | Greco et al. |
| 2003/0176873 | A1 | 9/2003 | Chernenko et al. |
| 2003/0229370 | A1 | 12/2003 | Miller |
| 2004/0006333 | A1 | 1/2004 | Arnold et al. |
| 2004/0010249 | A1 | 1/2004 | Truckai et al. |
| 2004/0044308 | A1 | 3/2004 | Naimark et al. |
| 2004/0097963 | A1 | 5/2004 | Seddon |
| 2004/0097996 | A1 | 5/2004 | Rabiner et al. |
| 2004/0162508 | A1 | 8/2004 | Uebelacker |
| 2004/0249401 | A1 | 12/2004 | Rabiner et al. |
| 2004/0254570 | A1 | 12/2004 | Hadjicostis et al. |
| 2005/0015953 | A1 | 1/2005 | Keidar |
| 2005/0021013 | A1 | 1/2005 | Visuri et al. |
| 2005/0059965 | A1 | 3/2005 | Eberl et al. |
| 2005/0075662 | A1 | 4/2005 | Pedersen et al. |
| 2005/0090888 | A1 | 4/2005 | Hines et al. |
| 2005/0113722 | A1 | 5/2005 | Schultheiss |
| 2005/0113822 | A1 | 5/2005 | Fuimaono et al. |
| 2005/0171527 | A1 | 8/2005 | Bhola |
| 2005/0228372 | A1 | 10/2005 | Truckai et al. |
| 2005/0245866 | A1 | 11/2005 | Azizi |
| 2005/0251131 | A1 | 11/2005 | Lesh |
| 2006/0004286 | A1 | 1/2006 | Chang et al. |
| 2006/0069424 | A1 | 3/2006 | Acosta et al. |
| 2006/0074484 | A1 | 4/2006 | Huber |
| 2006/0184076 | A1 | 8/2006 | Gill et al. |
| 2006/0190022 | A1 | 8/2006 | Beyar et al. |
| 2006/0221528 | A1 | 10/2006 | Li et al. |
| 2007/0016112 | A1 | 1/2007 | Schultheiss et al. |
| 2007/0088380 | A1 | 4/2007 | Hirszowicz et al. |
| 2007/0129667 | A1 | 6/2007 | Tiedtke et al. |
| 2007/0156129 | A1 | 7/2007 | Kovalcheck |
| 2007/0239082 | A1 | 10/2007 | Schultheiss et al. |
| 2007/0239253 | A1 | 10/2007 | Jagger et al. |
| 2007/0244423 | A1 | 10/2007 | Zumeris et al. |
| 2007/0250052 | A1 | 10/2007 | Wham |
| 2007/0255270 | A1 | 11/2007 | Carney |
| 2007/0282301 | A1 | 12/2007 | Segalescu et al. |
| 2007/0299481 | A1 | 12/2007 | Syed et al. |
| 2008/0097251 | A1 | 4/2008 | Babaev |
| 2008/0188913 | A1 | 8/2008 | Stone et al. |
| 2009/0041833 | A1 | 2/2009 | Bettinger et al. |
| 2009/0227992 | A1 | 9/2009 | Nir et al. |
| 2009/0230822 | A1 | 9/2009 | Kushculey et al. |
| 2009/0247945 | A1 | 10/2009 | Levit et al. |
| 2009/0254114 | A1 | 10/2009 | Hirszowicz et al. |
| 2009/0299447 | A1 | 12/2009 | Jensen et al. |
| 2009/0312768 | A1 | 12/2009 | Hawkins et al. |
| 2010/0016862 | A1 | 1/2010 | Hawkins et al. |
| 2010/0036294 | A1 | 2/2010 | Mantell et al. |
| 2010/0094209 | A1 | 4/2010 | Drasler et al. |
| 2010/0114020 | A1 | 5/2010 | Hawkins et al. |
| 2010/0114065 | A1 | 5/2010 | Hawkins et al. |
| 2010/0121322 | A1 | 5/2010 | Swanson |
| 2010/0179424 | A1 | 7/2010 | Warnking et al. |
| 2010/0286709 | A1 | 11/2010 | Diamant et al. |
| 2010/0305565 | A1 | 12/2010 | Truckai et al. |
| 2011/0034832 | A1 | 2/2011 | Cioanta et al. |
| 2011/0118634 | A1 | 5/2011 | Golan |
| 2011/0208185 | A1 | 8/2011 | Diamant et al. |
| 2011/0257523 | A1 | 10/2011 | Hastings et al. |
| 2011/0295227 | A1 | 12/2011 | Hawkins et al. |
| 2012/0071889 | A1 | 3/2012 | Mantell et al. |
| 2012/0095461 | A1 | 4/2012 | Herscher et al. |
| 2012/0116289 | A1 | 5/2012 | Hawkins et al. |
| 2012/0143177 | A1 | 6/2012 | Avitall et al. |
| 2012/0157991 | A1 | 6/2012 | Christian |
| 2012/0203255 | A1 | 8/2012 | Hawkins et al. |
| 2012/0221013 | A1 | 8/2012 | Hawkins et al. |
| 2012/0253358 | A1 | 10/2012 | Golan et al. |
| 2013/0030431 | A1 | 1/2013 | Adams |
| 2013/0041355 | A1 | 2/2013 | Heeren et al. |
| 2013/0116714 | A1 | 5/2013 | Adams et al. |
| 2013/0123694 | A1 | 5/2013 | Subramaniyan et al. |
| 2013/0150874 | A1 | 6/2013 | Kassab |
| 2013/0253622 | A1 | 9/2013 | Hooven |
| 2014/0046229 | A1 | 2/2014 | Hawkins et al. |
| 2014/0214061 | A1 | 7/2014 | Adams et al. |
| 2015/0320432 | A1 | 11/2015 | Adams |
| 2016/0151081 | A1 | 6/2016 | Adams et al. |
| 2016/0324534 | A1 | 11/2016 | Hawkins et al. |
| 2017/0135709 | A1 | 5/2017 | Nguyen et al. |
| 2017/0311965 | A1 | 11/2017 | Adams |
| 2021/0085383 | A1 | 3/2021 | Vo et al. |
| 2021/0338258 | A1 | 11/2021 | Hawkins et al. |
| 2022/0015785 | A1 | 1/2022 | Hakala et al. |
| 2022/0240958 | A1 | 8/2022 | Nguyen et al. |
| 2023/0043475 | A1 | 2/2023 | Adams |
| 2023/0293197 | A1 | 9/2023 | Nguyen et al. |
| 2023/0310073 | A1 | 10/2023 | Adams et al. |
| 2023/0329731 | A1 | 10/2023 | Hakala et al. |

FOREIGN PATENT DOCUMENTS

| | | | |
|---|---|---|---|
| CA | 2104414 | A1 | 2/1995 |
| CN | 1204242 | A | 1/1999 |
| CN | 1269708 | A | 10/2000 |
| CN | 1942145 | A | 4/2007 |
| CN | 101043914 | A | 9/2007 |
| CN | 102057422 | A | 5/2011 |
| CN | 102271748 | A | 12/2011 |
| CN | 102355856 | A | 2/2012 |
| CN | 102765785 | A | 11/2012 |
| CN | 203564304 | U | 4/2014 |
| DE | 3038445 | A1 | 5/1982 |
| DE | 202006014285 | U1 | 12/2006 |
| EP | 0442199 | A2 | 8/1991 |
| EP | 0571306 | A1 | 11/1993 |
| EP | 623360 | A1 | 11/1994 |
| EP | 647435 | A1 | 4/1995 |
| EP | 2253884 | A1 | 11/2010 |
| EP | 2362798 | B1 | 4/2014 |
| JP | S62-099210 | U | 6/1987 |
| JP | S62-275446 | A | 11/1987 |
| JP | H03-63059 | A | 3/1991 |
| JP | H06-125915 | A | 5/1994 |
| JP | H01-47135 | A | 2/1995 |
| JP | H08-89511 | A | 4/1996 |
| JP | H10-99444 | A | 4/1998 |
| JP | H10-314177 | A | 12/1998 |
| JP | H10-513379 | A | 12/1998 |
| JP | 2002538932 | A | 11/2002 |

(56) References Cited

FOREIGN PATENT DOCUMENTS

| | | | |
|---|---|---|---|
| JP | 2004081374 | A | 3/2004 |
| JP | 2004357792 | A | 12/2004 |
| JP | 2005501597 | A | 1/2005 |
| JP | 2005095410 | A | 4/2005 |
| JP | 2005515825 | A | 6/2005 |
| JP | 2006516465 | A | 7/2006 |
| JP | 2007289707 | A | 11/2007 |
| JP | 2007532182 | A | 11/2007 |
| JP | 2008506447 | A | 3/2008 |
| JP | 2011513694 | A | 4/2011 |
| JP | 2011520248 | A | 7/2011 |
| JP | 2011524203 | A | 9/2011 |
| JP | 2011528963 | A | 12/2011 |
| JP | 2012505050 | A | 3/2012 |
| JP | 2012508042 | A | 4/2012 |
| JP | 2015525657 | A | 9/2015 |
| JP | 2015528327 | A | 9/2015 |
| JP | 6029828 | B2 | 11/2016 |
| JP | 6081510 | B2 | 2/2017 |
| WO | WO-1989011307 | A1 | 11/1989 |
| WO | WO-1996024297 | A1 | 8/1996 |
| WO | WO-1999000060 | A1 | 1/1999 |
| WO | WO-1999002096 | A1 | 1/1999 |
| WO | WO-2000056237 | A2 | 9/2000 |
| WO | WO-2004069072 | A2 | 8/2004 |
| WO | WO-2005099594 | A1 | 10/2005 |
| WO | WO-2005102199 | A1 | 11/2005 |
| WO | WO-2006006169 | A2 | 1/2006 |
| WO | WO-2006127158 | A2 | 11/2006 |
| WO | WO-2007088546 | A2 | 8/2007 |
| WO | WO-2007149905 | A2 | 12/2007 |
| WO | WO-2009121017 | A1 | 10/2009 |
| WO | WO-2009126544 | A1 | 10/2009 |
| WO | WO-2009136268 | A1 | 11/2009 |
| WO | WO-2009152352 | A2 | 12/2009 |
| WO | WO-2010014515 | A2 | 2/2010 |
| WO | WO-2010054048 | A2 | 5/2010 |
| WO | WO-2011006017 | A1 | 1/2011 |
| WO | WO-2011094111 | A2 | 8/2011 |
| WO | WO-2011143468 | A2 | 11/2011 |
| WO | WO-2012025833 | A2 | 3/2012 |
| WO | WO-2013059735 | A1 | 4/2013 |
| WO | WO-2014025397 | A1 | 2/2014 |
| WO | WO-2014025620 | A1 | 2/2014 |
| WO | WO-2014043400 | A1 | 3/2014 |
| WO | WO-2015017499 | A1 | 2/2015 |
| WO | WO-2019099218 | A1 | 5/2019 |

OTHER PUBLICATIONS

"Top Cardiovascular Innovation Award", Cardiovascular Research Technologies (CRT), 2015, p. 1.

Achim et al., "Applications of shock waves in medicine", Handbook of Shock Waves. Academic Press, 2001, pp. 1-80.

Advisory Action received for U.S. Appl. No. 12/482,995, mailed on Jun. 2, 2014, 3 pages.

Advisory Action received for U.S. Appl. No. 12/482,995, mailed on Sep. 29, 2011, 2 pages.

Advisory Action received for U.S. Appl. No. 12/581,295, mailed on Jul. 3, 2014, 3 pages.

Advisory Action received for U.S. Appl. No. 13/049,199, mailed on Jun. 7, 2012, 3 pages.

Advisory Action received for U.S. Appl. No. 13/267,383, mailed on Jan. 6, 2014, 4 pages.

Advisory Action received for U.S. Appl. No. 13/615,107, mailed on Nov. 6, 2015, 3 pages.

Affirmance of FWD under Fed. Cir. R. 36, United States Court of Appeals for the Federal Circuit, dated Jan. 18, 2022 (Affirmance), 2 pages.

Akiyama et al., "Current-voltage characteristics of a high-current pulsed discharge in air", IEEE, Apr. 1988, 1 page.

Annotated Diagram from 8,728,091 Patent, May 20, 2014, 1 page.

Ardley, T., (2008). "First Principles of a Gas Discharge Tube (GOT) Primary Protector", Bourns, Rev. 2, Available Online at <https://www.mouser.com/pdfdocs/bourns_gdt_white_paper.pdf>, pp. 1-34.

Armstrong Ehrin, "Responses to Question 6 by Patent Owner's Declarants Ehrin Armstrong", Jan. 29, 2020, 5 pages.

Armstrong Ehrin, "Responses to Questions 1-5 by Patent Owner's Declarants Ehrin Armstrong", Jan. 24, 2020., 4 pages.

Bank of America Merrill Lynch, (2019). "A Simple Solution to a Difficult (and Large) Problem—Initiating Coverage of SWAY", Shockwave Medical Inc., pp. 1-22.

Barkhordarian, Vrej, "Power Mosfet basics", Powerconversion and Intelligent Motion-English Edition, 1996, pp. 1-13.

Bittl et al., (1993). "Coronary Artery Perforation during Excimer Laser Coronary Angioplasty", Journal of the American College of Cardiology, 21(5):1158-1165.

Bittl et al., (1993). "Publication Information—Coronary Artery Perforation during Excimer Laser Coronary Angioplasty", Journal of the American College of Cardiology, 21(5):1158-1165, 6 pages.

Breakthrough Devices Program Guidance for Industry and Food and Drug Administration Staff, U.S. Food & Drug Administration, Dec. 18, 2018.

Brinton et al., (2016). "Publication Information—TCT-777 Safety and Performance of the Shockwave Medical Lithoplasty® System in Treating Calcified Peripheral Vascular Lesions: 6-Month Results from the Two-Phase Disrupt Pad Study", Journal of the American College of Cardiology, 68(18): Supplement, 5 pages.

Brinton et al., (2016). "TCT-777 Safety and Performance of the Shockwave Medical Lithoplasty® System in Treating Calcified Peripheral Vascular Lesions: 6-Month Results from the Two-Phase Disrupt Pad Study", Journal of the American College of Cardiology, vol. 68, No. 18, Supplement B, p. B314.

Brinton, et al., "Feasibility of Shockwave Coronary Intravascular Lithotripsy for the Treatment of Calcified Coronary Stenoses", Circulation, vol. 139, Feb. 5, 2019, pp. 1-2.

Broyer et al., (1996). "High-Efficiency Shock-Wave Generator for Extracorporeal Lithotripsy", Medical and Biological Engineering and Computing, 34:321-328.

By et al., "Compliant vs Non-Compliant Balloons", Japanese Heart Journal, vol. 39, No. 1, 1998, 1 page.

Cardiology Today's Intervention, (2019). "Shockwave Attracts Additional Investment from Abiomed, has IPO", Available Online at <https://www.healio.com/cardiac-vascular intervention/peripheral/news/online/%7Bf96c1e20-b4a9-4167-bdb8-254e86a81 82a%7D/shockwave-attracts-additional-investment-from-abiomed-has-ipo>, pp. 1-2.

Cavanaugh, Kennethj. "Shockwave Intravascular Lithotripsy System with the Shockwave C2 Coronary IVL Catheter", U.S. Food & Drug Administration, Center for Devices and Radiological Health., Aug. 19, 2019, 2 pages.

Challenging Calcium Made Shockingly Easy, Shockwave IVL, 2019, 4 pages.

Citel Inc., "Gas Discharge Overview", Available Online at <http://www.citel.us/gas_discharge_tubes_overview.html>, pp. 1-2.

Claim Chart showing correspondence between the claims of U.S. Pat. No. 8,728,091 and the Shockwave C2 Device, 2020, 6 pages.

Claim Chart showing correspondence between the claims of U.S. Pat. No. 8,728,091 and the Shockwave M5 Device, 2020, 6 pages.

Claim Chart showing correspondence between the claims of U.S. Pat. No. 8,728,091 and the Shockwave S4 Device, 2020, 6 pages.

Clara, Santa, "Shockwave Medical Reports Second Quarter 2019 Financial Results", Globe Newswire, Aug. 5, 2019, 3 pages.

Cleveland et al., (2000). "Design and Characterization of a Research Electrohydraulic Lithotripter Patterned after the Dornier HM3", Review of Scientific Instruments, 71(6):2514-2525.

Cleveland et al., (2012). "The Physics of Shock Wave Lithotripsy", Extracorporeal Shock Wave Lithotripsy Part IV, Chapter 38, pp. 317-332.

Concise Description of Relevance Accompanying Third Party Preissuance Submission Under 37 CFR 1.290 for U.S. Appl. No. 16/694,712, filed Apr. 10, 2020, 27 pages.

Connors et al., (2003). "Renal Nerves Mediate Changes in Contralateral Renal Blood Flow after Extracorporeal Shockwave Lithotripsy", Nephron Physiol., 95:67-75.

(56) References Cited

OTHER PUBLICATIONS

CoolMOS 1) Power MOSFET Advanced Technical Information IXKR 47N60C5, IXYS, 2008, pp. 1-5.
Coronary Intravascular Lithotripsy (IVL) System Instructions for Use (IFU), Shockwave C2., May 2018, pp. 1-48.
Coronary IVL System Step-by-Step Setup, Shockwave C2, 2018, pp. 1-11.
Coronary Tech Sheet, Shockwave C2, 2018, pp. 1-2.
Deagon, Brian Technology—Shockwave Medical IPO Soars on First Day of Trading Investor's Business Daily, Available Online at <https://www.investors.com/news/technology/shockwave-medical-ipo-soars-trading/> Mar. 7, 2019, pp. 1-15.
Decision for U.S. Pat. No. 8,728,091, by the Patent Trial and Appeal Board dated Jul. 11, 2020, IPR2019-00409, Jul. 11, 2020, pp. 1-72.
Decision of Inter Partes Review for U.S. Pat. No. 8,728,091, by the Patent Trial and Appeal Board dated Jul. 11, 2019, pp. 1-32.
Decision to Grant received for European Patent Application No. 13756766.5, mailed on May 27, 2016, 2 pages.
Decision to Grant received for Japanese Patent Application No. 2011-513694, mailed on Oct. 7, 2014, 3 pages.
Declaration and Curriculum Vitae of Dr. Daniel W. Van Der Weide, Case IPR2019-00409, 2020, 148 pages.
Declaration of Dean Kereiakes, Case IPR2019-00409, Oct. 31, 2019, 12 pages.
Declaration of Dr. Morten Olgaard Jensen, Dec. 6, 2018, 138 pages.
Declaration of Ehrin J. Armstrong, Nov. 2, 2019, 69 pages.
Declaration of Jonathan M. Hill, Case IPR2019-00409, Mar. 11, 2019, 32 pages.
Declaration of Natalie J. Grace on Apr. 14, 2019, pp. 1-5.
Declaration of Natalie J. Grace, Case IPR2019-00409, Nov. 3, 2019, 9 pages.
Declaration of Peter Soukas, Case IPR2019-00409, Nov. 2016, 66 pages.
Declaration of Sean Lyden, Case IPR2019-00409, Oct. 31, 2019, 12 pages.
Declaration of William Patrick Stephens on Apr. 14, 2019, pp. 1-6.
Declaration of William Patrick Stephens, Case IPR2019-00409, Nov. 2, 2019, 4 pages.
Deposition Exhibit from Deposition of Dr. Jensen, Handwritten Diagram, Feb. 24, 2020, 1 page.
Deposition of Peter Soukas, Case TPR2019-00405, Nov. 2016, pp. 1-66.
Deposition Transcript (compressed) of Daniel van der Weide, Case No. IPR2019-00409, Jan. 10, 2020, 111 pages.
Deposition Transcript (compressed) of Dr. Morten Olgaard Jensen in Case No. IPR2019- 00409, Oct. 14, 2019., pp. 1-90.
Deposition Transcript (compressed) of Dr. Morten Olgaard Jensen, Case No. IPR2019- 00409, Feb. 24, 2020, pp. 1-82.
Deposition Transcript (compressed) of Ronald David Berger, Case No. IPR2019-00405, Jan. 27, 2020., 103 pages.
Diagram, Deposition Exhibit from Deposition of Dr. Jensen, Feb. 24, 2020, 1 page.
Dill, et al., "A randomized comparison of balloon angioplasty versus rotational atherectomy in complex coronary lesions (COBRA study)", European Heart Journal, vol. 21, No. 21, Oct. 2000, pp. 1-2.
Dodd, A. T. S., (1842). "Two Cases of Calculus in the Bladder, in which Lithotripsy was Performed", Provincial Medical & Surgical Journal, 3(71):368-370.
Dr. Jensen, "Dr. Jensen's drawings of his opinion of a typical symbol for a gas discharge tube", Oct. 14, 2019, 1 page.
Dr. Jensen, "Eleg 2104—Electric Circuits I Course Syllabus", Feb. 24, 2020, pp. 1-2.
Dual Full Bridge PWM Motor Driver, Instruments, Texas., Jul. 2011, pp. 1-29.
Elmansy et al., (2016). "Publication Information—Recent Advances in Lithotripsy Technology and Treatment Strategies: A Systematic Review Update", International Journal of Surgery, vol. 36, Part D, pp. 1-6.
Elmansy et al., (2016). "Recent Advances in Lithotripsy Technology and Treatment Strategies: A Systematic Review Update", International Journal of Surgery, 36:676-680.
Email correspondence between parties and Patent Trial and Appeal Board, IPR2019- 00408; IPR2019-00409, Jan. 20, 2020, 3 pages.
Evidence of Ph.D. for Dr. Achim M. Loske, ORCID Connecting Research and Researchers, 2019, pp. 1-6.
Extended European Search Report (includes Supplementary European Search Report and Search Opinion) received for European Patent Application No. 09763640.1, mailed on Oct. 10, 2013, 5 pages.
Extended European Search Report received for European Patent Application No. 13827971.6, mailed on Apr. 12, 2016, 8 pages.
Extended European Search Report received for European Patent Application No. 21165848.9, mailed on Jun. 29, 2021, 6 pages.
Filed Under Seal—Parties & Board Only—Deposition Transcript (compressed) of Dr. Morten Olgaard Jensen, Case No. IPR2019-00408, Feb. 26, 2020., pp. 1-80.
Final Office Action received for U.S. Appl. No. 12/482,995, mailed on Feb. 20, 2014, 11 pages.
Final Office Action received for U.S. Appl. No. 12/482,995, mailed on Jul. 22, 2011, 14 pages.
Final Office Action received for U.S. Appl. No. 12/501,619, mailed on Feb. 21, 2012, 12 pages.
Final Office Action received for U.S. Appl. No. 12/581,295, mailed on Jun. 5, 2014, 14 pages.
Final Office Action received for U.S. Appl. No. 12/581,295, mailed on Mar. 28, 2013, 8 pages.
Final Office Action received for U.S. Appl. No. 13/049,199, mailed on Apr. 4, 2012, 10 pages.
Final Office Action received for U.S. Appl. No. 13/049,199, mailed on Aug. 11, 2014, 8 pages.
Final Office Action received for U.S. Appl. No. 13/267,383, mailed on May 28, 2015, 12 pages.
Final Office Action received for U.S. Appl. No. 13/267,383, mailed on Oct. 25, 2013, 8 pages.
Final Office Action received for U.S. Appl. No. 13/534,658, mailed on Aug. 23, 2016, 11 pages.
Final Office Action received for U.S. Appl. No. 13/615,107, mailed on Sep. 1, 2015, 9 pages.
Final Office Action received for U.S. Appl. No. 13/646,570, mailed on Dec. 23, 2014, 10 pages.
Final Office Action received for U.S. Appl. No. 14/271,342, mailed on Feb. 27, 2015, 7 pages.
Final Written Decision for U.S. Pat. No. 8,728,091, by the Patent Trial and Appeal Board dated Jul. 8, 2020, Jul. 8, 2020, pp. 1-72.
Gambihler et al., (1994). "Permeabilization of the Plasma Membrane of LI210 Mouse Leukemia Cells Using Lithotripter Shock Waves", The Journal of Membrane Biology, 141:267-275.
Gottlieb, Scott, "U.S. Department of Health and Human Services, Food and Drug Administration Report to Congress by Scott Gottlieb", Exhibit 1217, Sep. 30, 2018, 10 pages.
Grassi et al., (2012). "Novel Antihypertensive Therapies: Renal Sympathetic Nerve Ablation and Carotid Baroreceptor Stimulation", Curr Hypertens Rep, 14:567-572.
Grocela et al., (1997). "Intracorporeal Lithotripsy. Instrumentation and Development", Urologic Clinics of North America, 24(1):13-23.
Havanur Sanjay, "Power MOSFET Basics—Understanding Voltage Ratings", Application Note AN851, Jan. 12, 2017, 4 pages.
Hill, Jonathanm., "Deposition Transcript (compressed) of Jonathan M. Hill, M.D.", Exhibit 1211, Case No. IPR2019-00408, U.S. Pat. No. 9,642,673, Dec. 16, 2019., 63 pages.
How (not) to destroy a relay, Deposition Exhibit from Deposition of Dr. Jensen, Feb. 24, 2020, pp. 1-7.
Intention to Grant received for European Patent Application No. 13756766.5, mailed on Jan. 8, 2016, 5 pages.
International Preliminary Report on Patentability received for PCT Patent Application No. PCT/US2009/047070, mailed on Dec. 23, 2010, 7 pages.
International Preliminary Report on Patentability received for PCT Patent Application No. PCT/US2011/047070, mailed on Feb. 21, 2013, 7 pages.

(56) References Cited

OTHER PUBLICATIONS

International Preliminary Report on Patentability received for PCT Patent Application No. PCT/US2012/023172, mailed on Aug. 15, 2013, 6 pages.
International Preliminary Report on Patentability received for PCT Patent Application No. PCT/US2013/031805, mailed on Feb. 19, 2015, 11 pages.
International Preliminary Report on Patentability received for PCT Patent Application No. PCT/US2013/039987, issued on Nov. 20, 2014, 11 pages.
International Preliminary Report on Patentability received for PCT Patent Application No. PCT/US2013/048277, mailed on Jan. 8, 2015, 9 pages.
International Preliminary Report on Patentability received for PCT Patent Application No. PCT/US2013/055431, mailed on Feb. 26, 2015, 7 pages.
International Preliminary Report on Patentability received for PCT Patent Application No. PCT/US2013/059533, mailed on Mar. 26, 2015, 10 pages.
International Search Report and Written Opinion received for PCT Patent Application No. PCT/US2013/031805, mailed on May 20, 2013, 13 pages.
International Search Report and Written Opinion received for PCT Patent Application No. PCT/US2013/039987, mailed on Sep. 23, 2013, 15 pages.
International Search Report and Written Opinion received for PCT Patent Application No. PCT/US2013/048277, mailed on Oct. 2, 2013, 14 pages.
International Search Report and Written Opinion received for PCT Patent Application No. PCT/US2013/055431, mailed on Nov. 12, 2013, 9 pages.
International Search Report and Written Opinion received for PCT Patent Application No. PCT/US2013/059533, mailed on Nov. 7, 2013, 14 pages.
International Search Report received for PCT Patent Application No. PCT/US2009/047070, mailed on Jan. 19, 2010, 4 pages.
International Search Report received for PCT Patent Application No. PCT/US2012/023172, mailed on Sep. 28, 2012, 3 pages.
International Written Opinion received for PCT Patent Application No. PCT/US2011 /047070, mailed on May 1, 2012, 5 pages.
International Written Opinion received for PCT Patent Application No. PCT/US2012/023172, mailed on Sep. 28, 2012, 4 pages.
International Written Opinion received for PCT Patent Application No. PCT/US2009/047070, mailed on Jan. 19, 2010, 5 pages.
IXYS High Voltage Power MOSFET data sheet for IXTF1N450, IXYS Corporation, 2013, 7 pages.
Kaplan et al., (1993). "Healing after Arterial Dilatation with Radiofrequency Thermal and Nonthermal Balloon Angioplasty Systems", Journal of Investigative Surgery, 6:33-52.
Kereiakes, Deanj., "Deposition Transcript (compressed) of Dean J. Kereiakes", Exhibit 1213, Cases No. 2019-00405, 00408 and 00409, Jan. 7, 2020., 65 pages.
Knight, D. W., (2013). "Gas Discharge Tubes—Introduction", G3YNH. info, Available Online at <http://g3ynh.info/disch_tube/intro.html>, pp. 1-9.
Kodama et al., (2002). "Shock wave-mediated molecular delivery into cells", Biochimica et Biophysica Acta, vol. 1542, pp. 186-194.
Lauer et al., (1997). "Shock Wave Permeabilization as a New Gene Transfer Method", Gene Therapy, 4:710-715.
Llewellyn-Jones, (1963). "The Mechanism of Electrode Erosion in Electrical Discharges," Platinum Metals Review, 7(2):58-65.
Locher Ralphe. "On switching inductive loads with power transistors", IEEE Transactions on Industrial Electronics and Control Instrumentation 4, 1970, pp. 256-262.
Manousakas et al., (2009). "A High-Voltage Discharging System for Extracorporeal Shock-Wave Therapy", IFMBE Proceedings, 23:706-707.
Martov et al., "Comparative In Vitro Study of the Effectiveness of Nanosecond Electrical Pulse and Laser Lithotripters", Journal of Endourology, vol. 27, No. 10, Oct. 2013, 1 page.
Mills et al., (2019). "Cracking the Code on Calcium; Initiate with BUY, $39 Target", Canaccord Genuity—Capital Markets, US Equity Research, pp. 1-63.
Mitomo, Satoru, (2018). "Intravascular lithotripsy: A Novel Technology for Treating Calcified Coronary Stenoses", Cardiovascular News, Online Available at <https://cardiovascularnews.com/intravascular-lithotripsy-anovel-technology-for-treating-calcified-coronary-stenoses>, pp. 1-4.
Modern Dictionary of Electronics, Sixth Edition, 1984, 5 pages.
Motisan, (2011). "Relaxation Oscillator Using a Hydrogen Thyratron", PocketMagic, Available Online at <https://www.pocketmagic.net/relaxation-oscillator-using-a-hydrogenthyratron)>, pp. 1-5.
Narui et al., "A Spice model for simulating arc discharge loads", IEEE, Sep. 28-Oct. 4, 1991, 1 page.
NEUWAVE Microwave Ablation System, Johnson & Johnson Medical Devices Companies, Available at: (https://www.jnjmedicaldevices.com/en-us/product/neuwavemicrowave-ablation-system, 2019, 4 pages.
Nisonson et al., (1986). "Ambulatory Extracorporeal Shockwave Lithotripsy", Urology, 28(5):381-384.
Non-Final Office Action received for U.S. Appl. No. 12/482,995, mailed on Aug. 13, 2014, 10 pages.
Non-Final Office Action received for U.S. Appl. No. 12/482,995, mailed on Feb. 11, 2011, 27 pages.
Non-Final Office Action received for U.S. Appl. No. 12/482,995, mailed on Jul. 12, 2013, 11 pages.
Non-Final Office Action received for U.S. Appl. No. 12/501,619, mailed on Jan. 28, 2014, 10 pages.
Non-Final Office Action received for U.S. Appl. No. 12/501,619, mailed on Nov. 3, 2011, 10 pages.
Non-Final Office Action received for U.S. Appl. No. 12/581,295, mailed on Dec. 21, 2012, 9 pages.
Non-Final Office Action received for U.S. Appl. No. 12/581,295, mailed on Jan. 15, 2015, 14 pages.
Non-Final Office Action received for U.S. Appl. No. 12/581,295, mailed on Jun. 8, 2012, 9 pages.
Non-Final Office Action received for U.S. Appl. No. 12/581,295, mailed on Mar. 10, 2014, 11 pages.
Non-Final Office Action received for U.S. Appl. No. 13/049,199, mailed on Dec. 12, 2011, 10 pages.
Non-Final Office Action received for U.S. Appl. No. 13/049,199, mailed on Feb. 4, 2014, 8 pages.
Non-Final Office Action received for U.S. Appl. No. 13/267,383, mailed on Apr. 19, 2013, 6 pages.
Non-Final Office Action received for U.S. Appl. No. 13/267,383, mailed on Feb. 25, 2015, 9 pages.
Non-Final Office Action received for U.S. Appl. No. 13/465,264, mailed on Dec. 23, 2014, 13 pages.
Non-Final Office Action received for U.S. Appl. No. 13/465,264, mailed on Oct. 29, 2014, 13 pages.
Non-Final Office Action received for U.S. Appl. No. 13/534,658, mailed on Mar. 11, 2016, 12 pages.
Non-Final Office Action received for U.S. Appl. No. 13/615,107, mailed on Apr. 24, 2015, 9 pages.
Non-Final Office Action received for U.S. Appl. No. 13/646,570, mailed on Oct. 29, 2014, 10 pages.
Non-Final Office Action received for U.S. Appl. No. 13/646,583, mailed on Oct. 31, 2014, 8 pages.
Non-Final Office Action received for U.S. Appl. No. 14/061,554, mailed on Mar. 12, 2014, 14 pages.
Non-Final Office Action received for U.S. Appl. No. 14/079,463, mailed on Mar. 4, 2014, 9 pages.
Non-Final Office Action received for U.S. Appl. No. 14/218,858, mailed on Mar. 30, 2016, 13 pages.
Non-Final Office Action received for U.S. Appl. No. 14/271,276, mailed on Aug. 4, 2014, 7 pages.
Non-Final Office Action received for U.S. Appl. No. 14/271,342, mailed on Sep. 2, 2014, 6 pages.
Non-Final Office Action received for U.S. Appl. No. 14/515,130, mailed on Jan. 14, 2016, 16 pages.
Non-Final Office Action received for U.S. Appl. No. 15/065,607, mailed on Feb. 22, 2018, 8 pages.
Non-Final Office Action received for U.S. Appl. No. 15/347,486, mailed on Nov. 2, 2018, 8 pages.

(56) References Cited

OTHER PUBLICATIONS

Notice of Acceptance Received for Australian Patent Application No. 2009257368, mailed on Aug. 28, 2014, 2 pages.
Notice of Acceptance received for Australian Patent Application No. 2013315444, mailed on Jul. 26, 2017, 3 pages.
Notice of Allowance received for Canadian Patent Application No. 2,727,429, mailed on May 26, 2015, 1 page.
Notice of Allowance received for Canadian Patent Application No. 2,881,199, mailed on Mar. 22, 2021, 1 page.
Notice of Allowance received for Chinese Patent Application No. 201380047277.3, mailed on Nov. 6, 2017, 2 pages (Official Copy Only) (See Communication under 37 CFR § 1.98(a) (3)).
Notice of Allowance received for Japanese Patent Application No. 2015-532052, mailed on Jun. 25, 2018, 3 pages (Official Copy Only) (See Communication under 37 CFR § 1.98(a) (3)).
Notice of Allowance received for U.S. Appl. No. 12/482,995, mailed on Dec. 24, 2014, 6 pages.
Notice of Allowance received for U.S. Appl. No. 12/581,295, mailed on Jul. 10, 2015, 15 pages.
Notice of Allowance received for U.S. Appl. No. 12/581,295, mailed on Jul. 29, 2015, 7 pages.
Notice of Allowance received for U.S. Appl. No. 13/049,199, mailed on Dec. 15, 2014, 7 pages.
Notice of Allowance received for U.S. Appl. No. 13/049,199, mailed on Jan. 13, 2015, 4 pages.
Notice of Allowance received for U.S. Appl. No. 13/465,264, mailed on May 8, 2015, 7 pages.
Notice of Allowance received for U.S. Appl. No. 13/615,107, mailed on Dec. 31, 2015, 10pages.
Notice of Allowance received for U.S. Appl. No. 13/646,570, mailed on Mar. 11, 2015, 7 pages.
Notice of Allowance received for U.S. Appl. No. 13/777,807, mailed on May 19, 2015, 13 pages.
Notice of Allowance received for U.S. Appl. No. 13/831,543, mailed on Oct. 8, 2014, 14 pages.
Notice of Allowance received for U.S. Appl. No. 14/061,554, mailed on Apr. 25, 2014, 8 pages.
Notice of Allowance received for U.S. Appl. No. 14/079,463, mailed on Apr. 1, 2014, 5 pages.
Notice of Allowance received for U.S. Appl. No. 14/218,858, mailed on Aug. 26, 2016, 8 pages.
Notice of Allowance received for U.S. Appl. No. 14/271,276, mailed on Feb. 25, 2015, 8 pages.
Notice of Allowance received for U.S. Appl. No. 14/271,342, mailed on Mar. 13, 2015, 5 pages.
Notice of Allowance received for U.S. Appl. No. 14/515,130, mailed on May 2, 2016, 8 pages.
Notice of Allowance received for U.S. Appl. No. 14/515,130, mailed on May 25, 2016, 3 pages.
Notice of Allowance received for U.S. Appl. No. 15/065,607, mailed on Aug. 10, 2018, 7 pages.
Notice of Allowance received for U.S. Appl. No. 15/347,486, mailed on Aug. 29, 2019, 7 pages.
Notice of Allowance received for U.S. Appl. No. 15/347,486, mailed on May 23, 2019, 8 pages.
Notice of Allowance received for U.S. Appl. No. 16/554,497, mailed on Nov. 14, 2019, 13 pages.
Notice of Allowance received for U.S. Appl. No. 16/694,712, mailed on May 4, 2022, 9 pages.
Notice of Opposition received for European Patent Application No. 21165848.9, mailed on May 5, 2024, 40 pages.
Office Action received for Australian Patent Application No. 2009257368, issued on Apr. 28, 2014, 4 pages.
Office Action received for Australian Patent Application No. 2009257368, issued on Jul. 31, 2013, 4 pages.
Office Action received for Australian Patent Application No. 2013315444, mailed on Nov. 30, 2016, 3 pages.
Office Action received for Canadian Patent Application No. 2,727,429, mailed on Apr. 14, 2015, 4 pages.
Office Action received for Chinese Patent Application No. 201380033808.3, mailed on Jul. 5, 2016, 9 pages.
Office Action received for Chinese Patent Application No. 201380041656.1, mailed on Jul. 5, 2016, 9 pages.
Office Action received for Chinese Patent Application No. 201380042887.4, mailed on Aug. 8, 2016, 9 pages.
Office Action received for Chinese Patent Application No. 201380047277.3, mailed on Aug. 19, 2016, 12 pages.
Office Action received for Chinese Patent Application No. 201380047277.3, mailed on Mar. 1, 2017, 10 pages.
Office Action received for Chinese Patent Application No. 201380047277.3, mailed on May 16, 2017, 13 pages.
Office Action received for Japanese Patent Application No. 2011-513694, mailed on Aug. 27, 2013, 6 pages.
Office Action received for Japanese Patent Application No. 2011-513694, mailed on Jun. 10, 2014, 4 pages.
Office Action received for Japanese Patent Application No. 2014-158517, mailed on May 19, 2015, 5 pages.
Office Action received for Japanese Patent Application No. 2015-532052, mailed on Aug. 21, 2017, 12 pages.
Office Action received for Japanese Patent Application No. 2015-532052, mailed on Feb. 6, 2018, 9 pages (6 pages of English Translation and 3 pages of Official Copy).
Opening Brief of Appellant Shockwave Medical, Inc. for Case No. 20-2251, dated Jan. 20, 2021, 159 pages.
Opening Brief of Appellee Cardiovascular Systems, Inc. for Case No. 20-2251, dated Mar. 31, 2021, 72 pages.
Operator's Manual, "Intravascular Lithotripsy (IVL) Generator and Connector Cable", LBL 61876 Rev. E, Mar. 2018, pp. 1-16.
Patent Owner Preliminary Response for U.S. Pat. No. 8,728,091, by the Patent Trial and Appeal Board dated Apr. 14, 2019, pp. 1-68.
Patent Owner's Response, Case No. IPR2019-00409, Nov. 3, 2019, 65 pages.
Patent Owner's Sur-Reply for U.S. Pat. No. 8,728,091, by the Patent Trial and Appeal Board dated Mar. 13, 2020, Case IPR2019-00409, Mar. 13, 2020, 30 pages.
Patents, ShockwaveMedical.com, 2019, 2 pages.
Patterson et al., (1985). "The Etiology and Treatment of delayed Bleeding following Percutaneous Lithotripsy", The Journal of Urology, 133: 447-451.
Peripheral Intravascular Lithotripsy (IVL) Catheter Instructions for Use (IFU), LBL 61932, Rev A Instructions for Use US, Jan. 2018, pp. 1-5.
Peripheral Intravascular Lithotripsy (IVL) Catheter Instructions for Use (IFU), LBL 61959, Rev. B Instructions for Use, Jun. 2018, pp. 1-7.
Petition for Inter Partes Review of U.S. Pat. No. 8,728,091, issued on May 20, 2014, 74 pages.
Petitioner's Reply Brief, Case IPR2019-00409, Feb. 14, 2020, 31 pages.
Pitchbook Profile Previews: Shockwave Medical, Available at: https://pitchbook.com/profiles/company/58446-10, 2019, pp. 1-3.
Prosecution History of U.S. Appl. No. 14/079,463, issued as U.S. Pat. No. 8,728,091, 860 pages.
Publicly available Professional & Educational Background Summary for (Michelle) Li., Exhibit 1225, 2018, 1 page.
Publicly available Professional & Educational Background Summary for Clifton Alferness, Exhibit 1229, 2013, 3 pages.
Publicly available Professional & Educational Background Summary for Dale Skelton, Exhibit 1228, 2013, 3 pages.
Publicly available Professional & Educational Background Summary for Daniel Hawkins, Exhibit 1226, 2018, 2 pages.
Publicly available Professional & Educational Background Summary for Doug Hakala, Exhibit 1222, 2016, 5 pages.
Publicly available Professional & Educational Background Summary for John Adams, Exhibit 1221, 2009, 2 pages.
Publicly available Professional & Educational Background Summary for Mauricio Jochinsen, 2010, 4 pages.
Publicly available Professional & Educational Background Summary for Randy Holmberg, Exhibit 1223, 2014, 3 pages.
Publicly available Professional & Educational Background Summary for Tammo Heeren, Exhibit 1224, 2018, pp. 1-2.

(56) References Cited

OTHER PUBLICATIONS

Publicly available Professional & Educational Background Summary for Valery Diamant, Exhibit 1257, 2017, 2 pages.
Ricks, Delthia, (2019). "Long Island Doctors Using Sound Waves to Loosen Calcium Deposits from Arteries, Restore Blood Flow", News/Health, Available Online at <https://www.newsday.com/news/health/calcium-treatment-st-francis-hospital-1.27314331 >, pp. 1-4.
Rosenschein et al., (1992). "Shock-Wave Thrombus Ablation, a New Method for Noninvasive Mechanical Thrombolysis", The American Journal of Cardiology, vol. 70, pp. 1358-1361.
Shockwave Announces Pricing of Initial Public Offering, News Release Details, Mar. 6, 2019, 2 pages.
Shockwave Medical Reports Fourth Quarter and Full Year 2019 Financial Results and Provides Full Year 2020 Financial Outlook, News Release Details, Feb. 13, 2020, 5 pages.
ShockWave Medical, Inc. (SWAV), Yahoo! Finance, Nov. 1, 2019, pp. 1-3.
Shockwavemedical.com, (2019). "Intravascular Lithotripsy (IVL)", Available Online at <https://shockwavemedical.com/technology/intravascular-lithotripsy-ivl/?country=Egypt>, pp. 1-4.
Soukas Peter, "Deposition Transcript of Peter Soukas," Cases: IPR2019-00405, IPR2019-00408, IPR2019-00409, Dec. 30, 2019, 81 pages.
Soukas, et al., "IVL for calcium: when does it work?", Presentation Slides for TCT 2019, TCTMD, 2019, pp. 1-87.
Speights Keith, "5 Top Medical Device Stocks to Buy Now", Aug. 3, 2019, pp. 1-15.
ST data sheet and specifications for STW9N150 Power MESH Power Mosfet, www.st.com, Jan. 2008, 12 pages.
Stephens William, "Deposition Transcript (compressed) of William Patrick Stephens", Case No. IPR2019-00408, Jan. 22, 2020, 55 pages.
Stone, Gregg, "Chapter 2: Use of IVL to Maintain Transfemoral TAVR Access", Partial Video Transcript of Shockwave TCTMD Roundtable, Accessible at <https://rutherfordmedicine.com/videos/Chapter-2-Use-Of-Ivl-To-Maintain-Transfe-F53891BD1>, 2020, 1 page.
Stone, Gregg, "Chapter 4: Current Trends, Best Practices & Updates with Peripheral IVL", Partial Video Transcript of Shockwave TCTMD Roundtable, Accessible at <https://rutherfordmedicine.com/videos/Chapter-4-Current-Trends-Best-Practices-95444B7E1>, 2020, 2 pages.
Stone, Gregg, "Chapter 6: IVL Roundtable Summary & Key Takeaways", Partial Video Transcript of Shockwave TCTMD Roundtable, 2020, 1 page.
Stone, Gregg, "Insights from EU Coronary Use & Overview of DISRUPT CAD III St", Partial Video Transcript of Shockwave TCTMD Roundtable, Accessible at <https://rutherfordmedicine.com/videos/Chapter-5-Insights-From-Eu-Coronary-Use-F6027EAA2>, 2020, 1 page.
Supplemental Declaration of Dr. Morten Olgaard Jensen, Case IPR2019-00409, U.S. Pat. No. 8,728,091 B2, Feb. 14, 2020, 54 pages.
Switching Inductive Loads, Deposition Exhibit from Deposition of Dr. Jensen, Feb. 24, 2020, 1 page.
Tanaka et al., (2001). "A New Radiofrequency Thermal Balloon Catheter for Pulmonary Vein Isolation", Journal of the American College of Cardiology, 38(7):2079-2086.
Texas Instruments, (2018). "Power Management Guide", Available Online at <http://www.ti.com/lit/sg/slvt145r/slvt145r.pdf>, pp. 1-93.
The American Heritage Dictionary of the English Language, New College Edition, 1978, 4 pages.
Third edition: Medical Design Standards for Power Supplies, International Standard, 2005, pp. 1-288.
Third Party Preissuance Submission for U.S. Appl. No. 16/694,712, filed Apr. 10, 2020, 3 pages.
Third-Party Submission Under 37 CFR 1.290 Concise Description of Relevance for U.S. Appl. No. 16/694,712, filed Apr. 10, 2020, 5 pages.
Transforming Breast Conserving Surgery Through Precise Surgical Navigation a Localization-Free Alternative, Elucent Medical, 2018, 1 page.
Tsuruta, et al., "A Model of Gas Temperature Decay After Arc Extinction of Small Air Gaps", Proceedings of the 3rd International Conference on Properties and Applications of Dielectric Materials, Jul. 8-12, 1991, pp. 1-4.
U.S. 2003/0176873, Chernenko et al., "Chernenko Drawings", Fig. 4b and Fig. 5 from Drawings as filed on Mar. 12, 2002, pp. 1-2.
Umemoto, et al., "TCT-362 A novel fully percutaneous thrombectomy technique with balloon occlusion guiding catheter and over-the-wire Fogarty catheter for acute limb ischemia", Journal of the American College of Cardiology, vol. 70, No. 18, 2017, 1 page.
United States Securities and Exchange Commission, Form 10-Q for ShockWave Medical, Inc., Aug. 6, 2019, pp. 1-39.
Webster's New Collegiate Dictionary, G. & C. Merriam Co, 1977., 4 pages.
Weide Daniel, "Deposition Transcript (compressed) of Daniel van der Weide, Ph.D.", Exhibit 1203, Case No. IPR2019-00408, U.S. Pat. No. 9,642,673 B2, Jan. 13, 2020, 94 pages.
Wells Fargo Securities LLC, (2019). "SWAY: Initiating With a Market Perform Rating", Shockwave Medical Inc., pp. 1-34.
Zhong et al., (1997) "Transient Oscillation of Cavitation Bubbles Near Stone Surface During Electrohydraulic Lithotripsy", Journal of Endourology, 11(1):55-61.
Zhong et al., (1997). "Publication Information—Transient Oscillation of Cavitation Bubbles Near Stone Surface During Electrohydraulic Lithotripsy", Journal of Endourology, 11(1):55-61, 1 page.
Ziad et al., "Safety and Effectiveness of Coronary Intravascular Lithotripsy for Treatment of Severely Calcified Coronary Stenoses", Circulation: Cardiovascular Intervention, 2019, pp. 1-29.

SHOCKWAVE CATHETER SYSTEM WITH ENERGY CONTROL

CROSS-REFERENCE TO RELATED APPLICATIONS

This application is a continuation of U.S. application Ser. No. 18/105,584, filed Feb. 3, 2023, which is a continuation of U.S. application Ser. No. 17/198,001, filed Mar. 10, 2021, issued as U.S. Pat. No. 11,596,424, on Mar. 7, 2023, which is a continuation of U.S. application Ser. No. 16/222,679, filed Dec. 17, 2018, issued as U.S. Pat. No. 10,973,538, on Apr. 13, 2021, which is a continuation of U.S. application Ser. No. 15/065,607, filed Mar. 9, 2016, issued as U.S. Pat. No. 10,159,505, on Dec. 25, 2018, which is a continuation of U.S. application Ser. No. 13/615,107, filed Sep. 13, 2012, issued as U.S. Pat. No. 9,333,000 on May 10, 2016, all entitled SHOCKWAVE CATHETER SYSTEM WITH ENERGY CONTROL, and each of which is hereby incorporated by reference in their entirety for all purposes.

BACKGROUND OF THE INVENTION

The present invention relates to a treatment system for percutaneous coronary angioplasty or peripheral angioplasty in which a dilation catheter is used to cross a lesion in order to dilate the lesion and restore normal blood flow in the artery. It is particularly useful when the lesion is a calcified lesion in the wall of the artery. Calcified lesions require high pressures (sometimes as high as 10-15 or even 30 atmospheres) to break the calcified plaque and push it back into the vessel wall. With such pressures comes trauma to the vessel wall which can contribute to vessel rebound, dissection, thrombus formation, and a high level of restenosis. Non-concentric calcified lesions can result in undue stress to the free wall of the vessel when exposed to high pressures. An angioplasty balloon when inflated to high pressures can have a specific maximum diameter to which it will expand but the opening in the vessel under a concentric lesion will typically be much smaller. As the pressure is increased to open the passage way for blood the balloon will be confined to the size of the opening in the calcified lesion (before it is broken open). As the pressure builds a tremendous amount of energy is stored in the balloon until the calcified lesion breaks or cracks. That energy is then released and results in the rapid expansion of the balloon to its maximum dimension and may stress and injure the vessel walls.

Recently, a new system and method has been contemplated for breaking up calcium deposits in, for example, arteries and veins. Such a system is described, for example in U.S. Patent Publication No. 2009/0312768, Published Dec. 17, 2009. Embodiments described therein include a catheter having balloon, such as an angioplasty balloon, at the distal end thereof arranged to be inflated with a fluid. Disposed within the balloon is a shock wave generator that may take the form of, for example, a pair of electrodes, which are coupled to a high voltage source at the proximal end of the catheter through a connector. When the balloon is placed adjacent a calcified region of a vein or artery and a high voltage pulse is applied across the electrodes, a shock wave is formed that propagates through the fluid and impinges upon the wall of the balloon and the calcified region. Repeated pulses break up the calcium without damaging surrounding soft tissue.

Each high voltage pulse causes an arc to form across the electrodes. The arc in turn causes a steam bubble to form. Each steam bubble has the potential of producing two shock waves, a leading edge shock wave as a result of bubble expansion and a trailing edge shock wave as a result of bubble collapse. The trailing edge shock waves exhibit highly variable energy levels and generally, much greater energy levels than the leading edge shock waves. The energy levels of the trailing edge shock waves are substantially dependent on the uniformity of the bubble collapse. The uniform collapse of spherical bubbles to a point appears to create the highest shock wave energies. Unfortunately, spherical bubble configuration requires a substantially larger space than is available in a balloon that must fit into a calcified vein or artery or even a ureter. In fact, the trailing edge shock wave can be substantially eliminated by confining the bubble to an irregular shape. As a result, for angioplasty or other cardiac and non-cardiac applications of shock waves, the trailing edge shock wave cannot be reliably relied upon to produce consistent results.

However, the leading edge shock waves formed by bubble expansion are a different matter. While exhibiting generally lower energies, they are more consistent in energy level. As a result, leading edge shock waves are good candidates for use in medical procedures such, for example, angioplasty or valvuloplasty.

Another consideration is the amount of energy represented by the high voltage applied to the electrodes. Each high voltage pulse removes a portion of the electrode material. Since the size of the electrodes must be small in order to fit into the calcified vein or artery, they are only capable of sustaining a limited numbers of high voltage pulses sufficient to form the shock wave resulting electrical arc.

Also, it has been learned that to sustain a leading edge shock wave, it is not necessary to sustain the high voltage throughout the shock wave. Sustaining the high voltage beyond some point after the initial arc does not lead to shock waves of any greater intensity. Further, since the bubbles are formed of steam, the steam produces heat which can increase the temperature of adjacent soft tissue. Just a two degree Celsius elevation in temperature above body temperature can result in tissue damage.

A still further important aspect of prior art attempts to use shock waves from electrical arcs for therapeutic purposes is that from the time the high voltage is first applied to the electrodes to the time in which the arc occurs there is a dwell time (Td) that is highly variable from one high voltage application to the next. To account for the dwell times that are long, prior art strategies have relied upon high voltage applications where all high voltage pulse durations or pulse widths are of the same length and of a length sufficient to extend through the longest of the anticipated dwell times plus the associated arc and steam bubble. As a result, when the dwell times are shorter than the maximum, the high voltage application durations are longer than necessary and can unnecessarily extend the arc and the steam bubble well beyond a time required to produce a shock wave of maximum intensity. The result is wasted energy, extended electrode erosion, and unnecessary heating of the adjoining tissue.

Hence, there is a need in the art to be able to control the energy applied to the electrodes of an electrical arc shock wave generator. More particularly, there is a need to control the applied energy to assure appropriate bubble and shock wave formation while at the same time conserving electrode material and assuring tissue safety. The present invention addresses these and other issues.

SUMMARY OF THE INVENTION

In one embodiment, a system includes a catheter including an elongated carrier and a balloon about the carrier in sealed relation thereto. The balloon is arranged to receive a fluid therein that inflates the balloon. The catheter further includes first and second electrodes within the balloon arranged to receive there-across a high electrical voltage at an initial low current. The high electrical voltage causes an electrical arc to form across the first and second electrodes within the balloon. The electrical arc creates a gas bubble within the liquid, a high current to flow through the first and second electrodes, and a mechanical shock wave within the balloon. The system further includes a power source that provides the first and second electrodes with the high electrical voltage at the initial current and that terminates the high electrical voltage in response to the high current flow through the first and second electrodes.

The power source includes a current sensor that senses current flowing through the first and second electrodes. The current sensor causes the power source to terminate the high electrical voltage when the current flowing through the first and second electrodes reaches a predetermined limit. The predetermined limit may be on the order of fifty amperes.

The system may further include a temperature sensor within the balloon that senses temperature of the fluid within the balloon. The power source may be further responsive to the temperature sensor.

The temperature sensor may cause the power source to decrease energy applied to the first and second electrodes responsive to the temperature of the fluid within the balloon increasing to control the temperature of the fluid. The temperature sensor may cause the power source to decrease energy applied to the first and second electrodes responsive to the temperature of the fluid within the balloon increasing to above two degrees Celsius above ambient temperature.

Each pulse of the serial electrical high voltage pulses has an amplitude. The temperature sensor may cause the power source to decrease the energy applied to the first and second electrodes by decreasing the amplitude of the serial electrical high voltage pulses. Alternatively, the temperature sensor may cause the power source to decrease the energy applied to the first and second electrodes by temporarily terminating the serial electrical high voltage pulses.

The serial electrical high voltage pulses have a pulse rate. The temperature sensor may cause the power source to decrease the energy applied to the first and second electrodes by decreasing the pulse rate of the serial electrical high voltage pulses.

The balloon may be a dilation balloon. The dilation balloon may be an angioplasty balloon. In some applications, such as lithotripsy, a balloon may not be required.

The system may further include a timer that times a delay time in response to the high current flow through the first and second electrodes and the power source may terminate the high electrical voltage after the delay time is timed. The power source may include a current sensor that senses current flowing through the first and second electrodes and the current sensor may cause the timer to time the delay time when the current flowing through the first and second electrodes reaches a predetermined limit. The predetermined limit may be on the order of fifty amperes.

In another embodiment, a system includes a catheter including an elongated carrier having a guide wire lumen and a balloon having an inner surface about the carrier in sealed relation thereto. The balloon forms a channel with the carrier. The channel is arranged to receive a fluid that inflates the balloon. The catheter further includes first and second electrodes within the balloon, between the carrier and the inner surface of the balloon, arranged to receive there-across a high electrical voltage at an initial low current to cause an electrical arc to form across the first and second electrodes within the balloon. The electrical arc creates a gas bubble within the liquid, a high current to flow through the first and second electrodes, and a mechanical shock wave within the balloon. The system further includes a power source that provides the first and second electrodes with the high electrical voltage at the initial current and that terminates the high electrical voltage in response to the high current flow through the first and second electrodes.

In a further embodiment, a system includes a catheter including an elongated carrier and a balloon about the carrier in sealed relation thereto. The balloon is arranged to receive a fluid therein that inflates the balloon. The catheter further includes first and second electrodes within the balloon arranged to receive there-across a high electrical voltage at an initial low current to cause an electrical arc to form across the first and second electrodes within the balloon. The electrical arc creates a steam bubble within the liquid, a high current to flow through the first and second electrodes, and a mechanical shock wave within the balloon. The steam bubble increases the temperature of the fluid. The system further includes a temperature sensor within the balloon that senses temperature of the fluid within the balloon and a power source that provides the first and second electrodes with the high electrical voltage at the initial current and that controls energy provided by the high electrical voltage in response to the sensed temperature of the fluid within the balloon.

The temperature sensor causes the power source to decrease energy applied to the first and second electrodes responsive to the temperature of the fluid within the balloon increasing to control the temperature of the fluid. The temperature sensor causes the power source to decrease energy applied to the first and second electrodes responsive to the temperature of the fluid within the balloon increasing to about two degrees Celsius above ambient temperature.

Each pulse of the serial electrical high voltage pulses has an amplitude. The temperature sensor may alternatively cause the power source to decrease the energy applied to the first and second electrodes by decreasing the amplitude of the serial electrical high voltage pulses. The temperature sensor may alternatively cause the power source to decrease the energy applied to the first and second electrodes by temporarily terminating the serial electrical high voltage pulses.

The serial electrical high voltage pulses have a pulse rate. The temperature sensor may alternatively cause the power source to decrease the energy applied to the first and second electrodes by decreasing the pulse rate of the serial electrical high voltage pulses.

The carrier of the catheter may have a guide wire lumen. The balloon has an inner surface that with the carrier, forms a channel arranged to receive the fluid that inflates the balloon. The first and second electrodes may be disposed between the carrier and the inner surface of the balloon.

According to a further embodiment, the invention provides a method that includes the steps of providing a catheter including an elongated carrier, a balloon about the carrier in sealed relation thereto, the balloon being arranged to receive a fluid therein that inflates the balloon, and first and second electrodes within the balloon. The method further includes introducing the fluid into the balloon to inflate the balloon, applying an electrical voltage across the first and second electrodes to form an electrical arc across the first and second electrodes, sensing current flow through the first and second electrodes, and varying the application of the electrical voltage across the first and second electrodes in response to sensed current flow through the first and second electrodes after the electrical arc is formed across the first and second electrodes.

The varying step may include terminating the application of the electrical voltage across the first and second electrodes. The high electrical voltage may be terminated when the current flowing through the first and second electrodes reaches a predetermined limit. The predetermined limit may be on the order of fifty amperes.

The method may include the further step of sensing temperature of the fluid within the balloon and the varying step may include varying the application of the electrical voltage across the first and second electrodes in response to sensed temperature of the fluid.

The varying step may include decreasing energy applied to the first and second electrodes responsive to the temperature of the fluid within the balloon increasing to control the temperature of the fluid. The energy applied to the first and second electrodes may be decreased responsive to the temperature of the fluid within the balloon increasing to above two degrees Celsius above ambient temperature.

The applying step may include applying energy in the form of serial electrical high voltage pulses and the varying step may further include decreasing the energy applied to the first and second electrodes by temporarily terminating the serial electrical high voltage pulses.

The serial electrical high voltage pulses have a pulse rate. Alternatively, the varying step may further include decreasing the energy applied to the first and second electrodes by decreasing the pulse rate of the serial electrical high voltage pulses.

The method may include the further step of timing a delay time in response to sensed current flow through the first and second electrodes and the varying step may include terminating the application of the electrical voltage across the first and second electrodes after timing the delay time. The delay time may be timed when the current flowing through the first and second electrodes reaches a predetermined limit. The predetermined limit may be on the order of fifty amperes.

According to another embodiment, a method includes the steps of providing a catheter including an elongated carrier, a balloon about the carrier in sealed relation thereto, the balloon being arranged to receive a fluid therein that inflates the balloon, and first and second electrodes within the balloon. The method further includes the steps of introducing the fluid into the balloon to inflate the balloon, applying energy in the form of an electrical voltage across the first and second electrodes to form an electrical arc across the first and second electrodes, sensing temperature of the fluid within the balloon, and varying the application of the energy across the first and second electrodes in response to sensed temperature of the fluid within the balloon.

The varying step may include decreasing the energy applied to the first and second electrodes responsive to the temperature of the fluid within the balloon increasing. The varying step may include decreasing the energy applied to the first and second electrodes responsive to the temperature of the fluid within the balloon increasing to about two degrees Celsius above ambient temperature.

Each pulse of the serial electrical high voltage pulses has an amplitude. The varying step may include decreasing the energy applied to the first and second electrodes by decreasing the amplitude of the serial electrical high voltage pulses.

The applying step may include applying energy in the form of serial electrical high voltage pulses and the varying step may further include decreasing the energy applied to the first and second electrodes by temporarily terminating the serial electrical high voltage pulses.

The applying step may include applying energy in the form of serial electrical high voltage pulses, wherein the serial electrical high voltage pulses have a pulse rate. The varying step may further include decreasing the energy applied to the first and second electrodes by decreasing the pulse rate of the serial electrical high voltage pulses.

In a still further embodiment, a system treats obstructions within bodily fluid and includes a catheter including first and second electrodes arranged to receive there-across a high electrical voltage at an initial low current. The high electrical voltage causes an electrical arc to form across the first and second electrodes. The electrical arc creates a gas bubble within the bodily fluid, a high current to flow through the first and second electrodes, and a mechanical shock wave within the bodily fluid. The system further includes a power source that provides the first and second electrodes with the high electrical voltage at the initial current and that terminates the high electrical voltage in response to the high current flow through the first and second electrodes.

The energy applied by the power source may be in the form of serial electrical high voltage pulses. Each pulse of the serial electrical high voltage pulses has an amplitude. The power source may control the energy applied to the first and second electrodes by varying the amplitude of the serial electrical high voltage pulses.

The serial electrical high voltage pulses have a pulse rate. Alternatively, the power source may vary the energy applied to the first and second electrodes by varying the pulse rate of the serial electrical high voltage pulses.

The system may further include a timer that times a delay time in response to the high current flow through the first and second electrodes and the power source may terminate the high electrical voltage after the delay time is timed. The power source may include a current sensor that senses current flowing through the first and second electrodes and the current sensor may cause the timer to time the delay time when the current flowing through the first and second electrodes reaches a predetermined limit. The predetermined limit may be on the order of fifty amperes.

In still a further embodiment, a method includes the steps of providing a catheter including first and second electrodes, applying an electrical voltage across the first and second electrodes to form an electrical arc across the first and second electrodes, sensing current flow through the first and second electrodes, and varying the application of the electrical voltage across the first and second electrodes in response to sensed current flow through the first and second electrodes after the electrical arc is formed across the first and second electrodes.

The applying step may include applying energy in the form of serial electrical high voltage pulses, the serial electrical high voltage pulses having a pulse rate, and wherein the varying step further includes controlling the energy applied to the first and second electrodes by varying the pulse rate of the serial electrical high voltage pulses.

The serial high voltage pulses have amplitudes. The varying step may alternatively or in addition include controlling the energy applied to the first and second electrodes by varying the amplitude of the serial electrical high voltage pulses.

The method may include the further step of timing a delay time in response to sensed current flow through the first and second electrodes and the varying step may include terminating the application of the electrical voltage across the first and second electrodes after timing the delay time. The delay time may be timed when the current flowing through the first and second electrodes reaches a predetermined limit. The predetermined limit may be on the order of fifty amperes.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

DETAILED DESCRIPTION OF THE INVENTION

Figure 1:
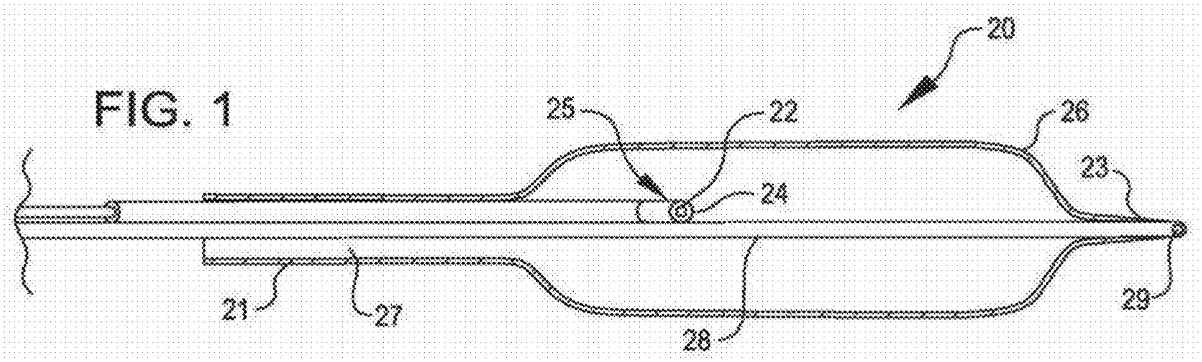
FIG. 1 is a simplified side view of an angioplasty balloon catheter of the type that may utilize various embodiments of the invention to advantage.

FIG. 1 is a simplified side view of an angioplasty balloon catheter 20 of the type that may utilize various embodiments of the invention to advantage. The catheter 20 includes an elongated carrier, such as a hollow sheath 21, a dilating balloon 26 formed about the sheath 21 in sealed relation thereto and a guide wire member 28 to which the balloon is sealed at a seal 23. The guide wire member has a longitudinal lumen 29 through which a guide wire (not shown) may be received for directing the catheter 20 to a desired location within a vein or artery, for example.

The sheath 21 forms with the guide wire member 28 a channel 27 through which fluid, such as saline, may be admitted into the balloon to inflate the balloon. The channel 27 further permits the balloon 26 to be provided with an electrode pair 25 including electrodes 22 and 24 within the fluid filled balloon 26.

Figure 2:
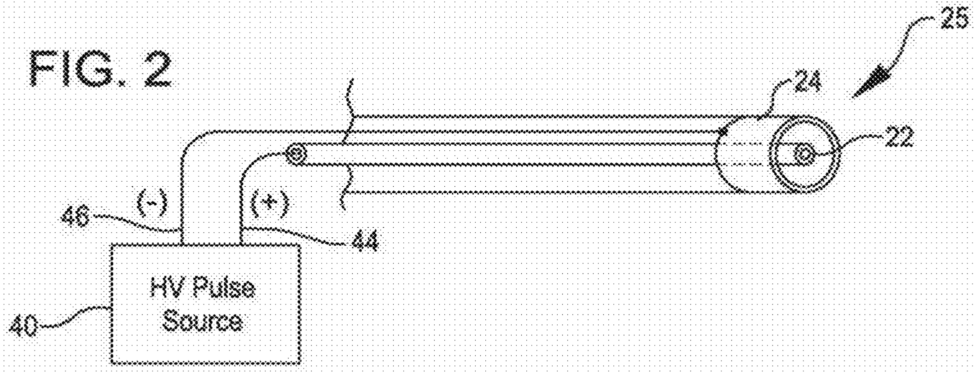
FIG. 2 is a simplified side view of an electrode structure that may be employed in the catheter of FIG. 1 coupled to a source of high voltage pulses according to one embodiment of the invention.
Figure 3:
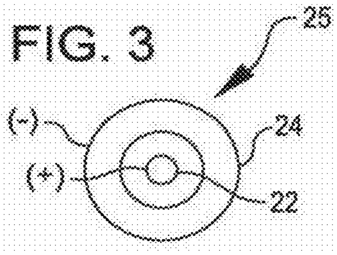
FIG. 3 is a front plan view of the electrode structure of FIG. 2.

As may be seen in FIG. 2, the electrodes 22 and 24 are attached to a source 40 of high voltage pulses. As may be seen in FIG. 3, the electrodes 22 and 24 are coaxially disposed with electrode 22 being a center electrode and electrode 24 being a ring shaped electrode about electrode 22. The center electrode 22 is coupled to a positive terminal 44 of source 40 and the ring electrode 24 is coupled to a negative terminal 46 of the source 40. The electrodes 22 and 24 are formed of metal, such as stainless steel, and are maintained a controlled distance apart to allow a reproducible arc to form for a given applied voltage and current.

The electrical arcs between electrodes 22 and 24 in the fluid are used to generate shock waves in the fluid. Each pulse of high voltage applied to the electrodes 22 and 24 forms an arc across the electrodes. The voltage pulses may have amplitudes as low as 500 volts, but preferably, the voltage amplitudes are in the range of 1000 volts to 10,000 volts The balloon 26 may be filled with water or saline in order to gently fix the balloon in the walls of the artery or vein, for example, in direct proximity with the calcified lesion. The fluid may also contain an x-ray contrast to permit fluoroscopic viewing of the catheter during use. Once the catheter 20 is positioned with the guide wire (not shown), the physician or operator can start applying the high voltage pulses to the electrodes to form the shock waves that crack the calcified plaque. Such shockwaves will be conducted through the fluid, through the balloon, through the blood and vessel wall to the calcified lesion where the energy will break the hardened plaque without the application of excessive pressure by the balloon on the walls of the artery.

Figure 4:
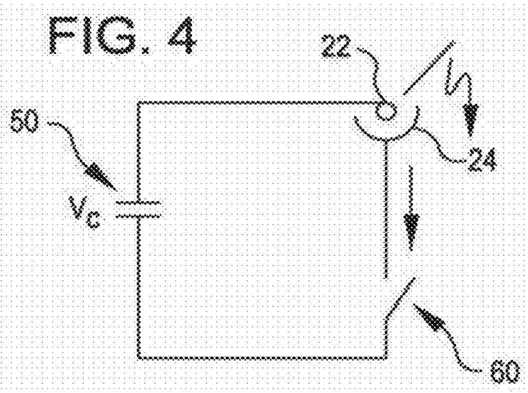
FIG. 4 is a simplified equivalent circuit diagram of a system according to an embodiment of the invention.

FIG. 4 is a simplified equivalent circuit diagram of a system according to an embodiment of the invention. Here it may be seen that a capacitance stores a high voltage. When a switch 60 is closed, the voltage drop across the electrodes 22 and 24 begins to quickly rise at an initially low current level. After a dwell time, when the voltage across the electrodes reaches the breakdown voltage of the fluid between the electrodes, an electrical arc occurs across the electrodes. The arc causes a steam bubble to form between the electrodes and a relatively high current to flow through the electrodes. The expansion of the bubble forms a first or leading edge shock wave. After a time, the steam bubble cools and condenses causing the bubble to collapse. The collapsing bubble has the potential for forming a second or trailing edge shock wave. As previously mentioned, the trailing edge shock wave is relatively unreliable exhibiting inconsistent intensities from shock wave to shock wave. Hence, it is the leading edge shock wave that holds the most promise for reliable therapy.

It has been found that effective shock wave intensity may be accomplished without holding the high voltage pulses on during the entire extent of their corresponding steam bubbles. Moreover, terminating the application of the high voltage before steam bubble collapse can serve to preserve electrode material, permitting a pair of electrodes to last for an increased number of applied high voltage pulses. Still further, as will be seen subsequently, early termination of the high voltage can also be used to advantage in controlling the temperature within the balloon fluid.

Figure 5:
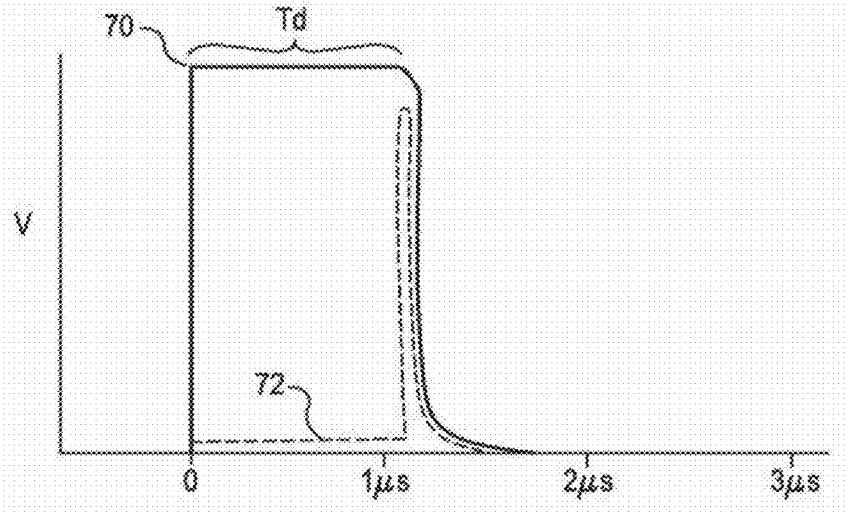
FIG. 5 is a graph illustrating a high voltage pulse applied to a pair of electrical arc shock wave producing electrodes and the resulting current flow through the electrodes in accordance with an embodiment of the invention.

FIG. 5 is a graph illustrating a high voltage pulse applied to a pair of electrical arc shock wave producing electrodes and the resulting current flow through the electrodes in accordance with an embodiment of the invention. When the switch 60 (FIG. 4) is first closed, the voltage across the electrodes quickly rises to a level 70. During this time, as shown by dashed lines 72, the current through the electrodes is relatively low. After a dwell time (Td), the arc occurs between the electrodes. At this time the steam bubble begins to form and a high current begins to flow through the electrodes. In accordance with embodiments of the invention, responsive to the current through the electrodes, the application of the high voltage is terminated. This conserves energy applied to the electrodes, causing the electrodes to remain useful for a greater number of pulses than otherwise would be the case if the high voltage were applied longer or sustained throughout the bubble existence. The advantages of controlling the applied energy in this manner are obtained without adversely affecting the intensity of the leading edge shock waves produced.

Figure 6:
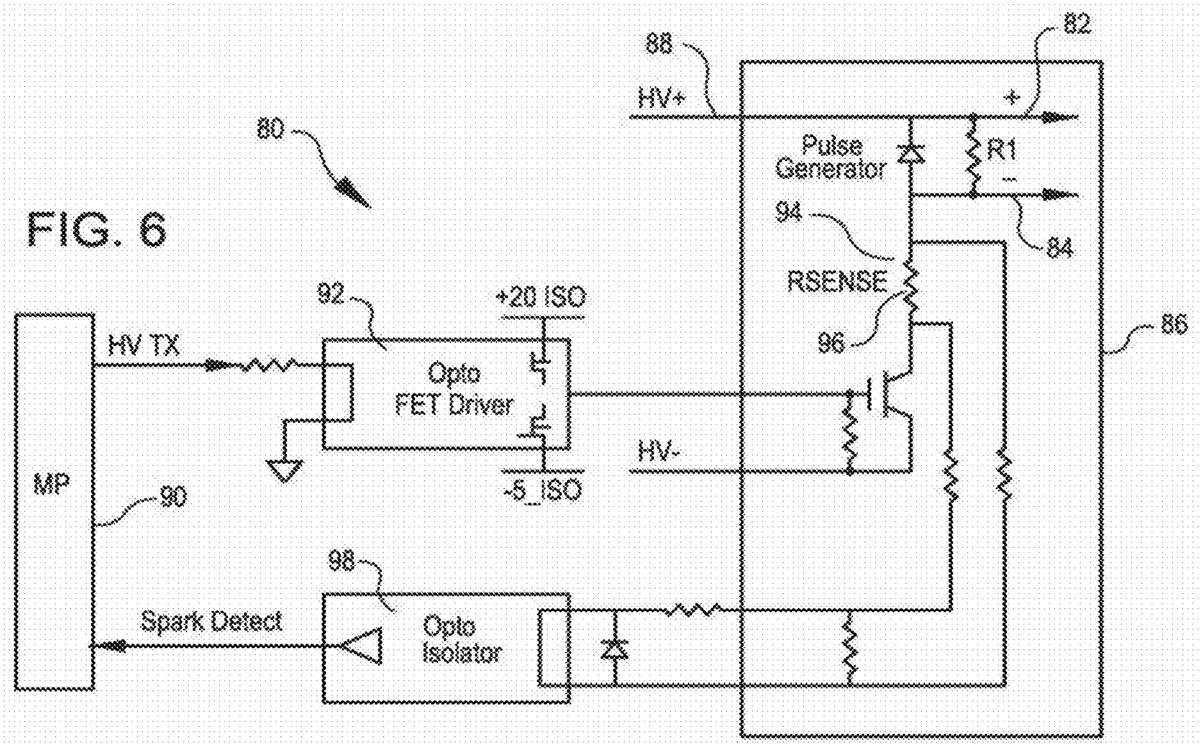
FIG. 6 is a schematic diagram of a power source for use in an angioplasty electrical arc shock wave angioplasty catheter according to an embodiment of the invention.

FIG. 6 is a schematic diagram of a power source 80 for use in an electrical arc shock wave angioplasty catheter according to an embodiment of the invention. The power source 80 has an output terminal 82 that may be coupled to electrode 22 of FIG. 1 and an output terminal 84 that may be coupled to electrode 24 of FIG. 1. A switch circuit 86 selectively applies a high voltage on line 88 across the electrodes. A microprocessor 90, or other similar control circuitry, such as a gate array, controls the overall operation of the source 80. A Field Programmable Gate Array (FPGA) may also be substituted for the microprocessor in a manner know in the art. The microprocessor 90 is coupled to the switch 86 by an optical driver 92. The switch includes a current sensor 94 that includes a current sensing resistor 96 that generates a signal that is applied to an optical isolator 98 when the current flowing through the electrodes reaches a predetermined limit, such as, for example, fifty (50) amperes.

In operation, the microprocessor 90 through the optical driver 92, causes the switch 86 to apply the high voltage to the electrodes 22 and 24. The current sensed through resister 96 is monitored by the microprocessor 90 through the optical isolator 98. When the current flowing through the electrodes reaches a predetermined limit, as for example 50 amperes, the microprocessor 90 causes the application of the high voltage to be terminated. The forgoing occurs for each high voltage pulse applied to the electrodes 22 and 24. Each pulse creates a shock wave of consistent and useful intensity. Further, because the application of the high voltage is terminated early, the electrode material is preserved to lengthen the useful life of the electrodes.

Figure 7:
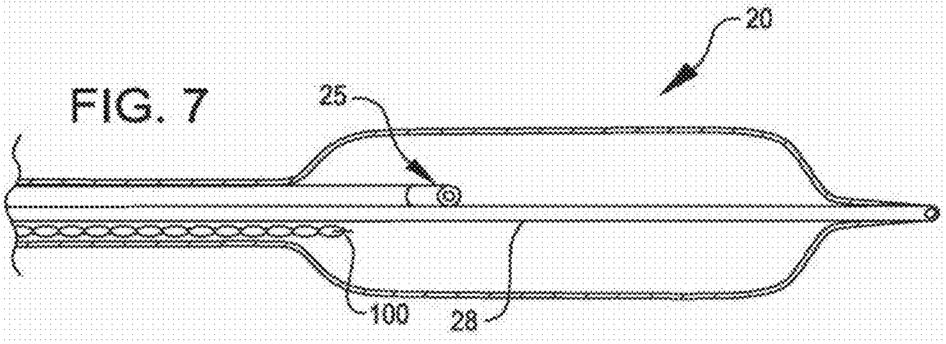
FIG. 7 is a side view of a dilating catheter with an electrical arc producing electrode structure and a temperature probe therein according to aspects of the invention.

FIG. 7 is a side view of a dilating catheter with an electrical arc producing electrode structure and a temperature probe therein according to aspects of the invention. The catheter 20 of FIG. 7 may be the same catheter as shown in FIG. 1. Here however, the catheter 20 further includes a temperature probe or sensor 100. The temperature sensor may be employed for sensing the temperature of the fluid within the balloon. Preferably, the temperature of the fluid within the balloon 26 should not be permitted to rise more than two degrees Celsius above the ambient body temperature. If this were to occur, soft tissue damage may result.

Figure 8:
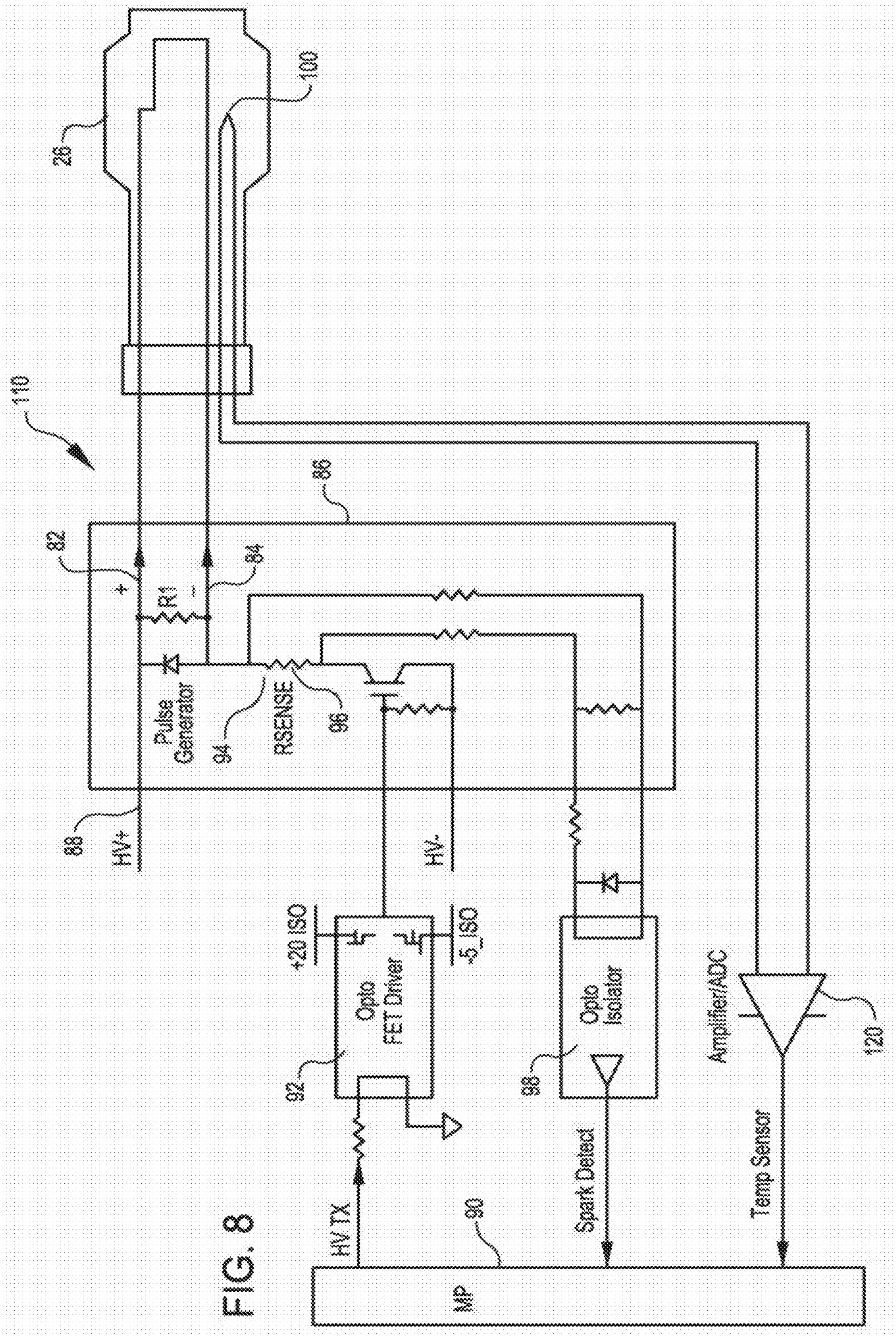
FIG. 8 is a schematic diagram of an angioplasty catheter system according to further embodiments of the invention.

FIG. 8 is a schematic diagram of an angioplasty catheter system 110 according to further embodiments of the invention which includes the catheter 20 and temperature probe 100. Here the system also includes the microprocessor 90, the switch 86, optical driver 92 and optical isolator 98. All of these elements may function as previously described. In addition, the temperature sensor 100 conveys a temperature signal through another optical isolator 120 indicative of the temperature of the fluid within the balloon 26. If the temperature within the balloon 26 rises to more than a certain temperature, for example to more than two degrees Celsius above ambient body temperature, the energy applied to the electrodes is decreased. This will decrease the size and duration of the steam bubbles produced by the electrodes to maintain the temperature of the fluid within the balloon to within safe limits. The microprocessor 90 may cause the switch 86 to decrease the pulse amplitude of the applied high voltage pulses or the pulse rate of the applied high voltage pulse. It could alternatively temporarily terminate the application of the pulses.

Figure 9:
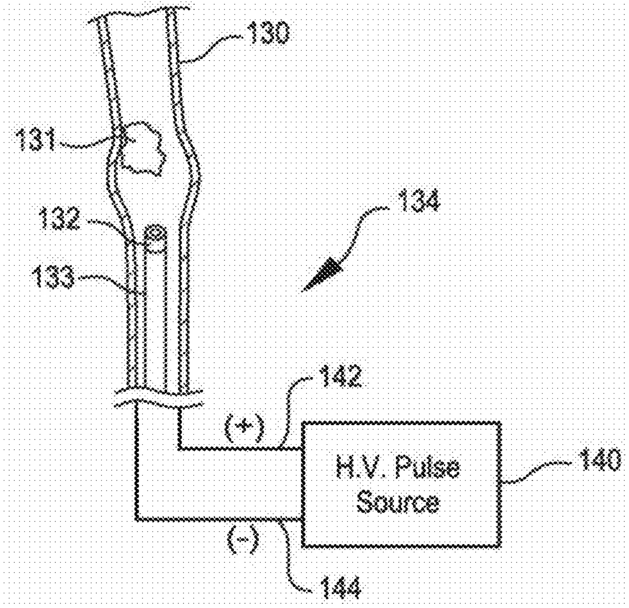
FIG. 9 is a simplified side view, partly in section, of a further embodiment wherein a balloon is not required.

FIG. 9 is a simplified side view, partly in section, of a further embodiment wherein a balloon is not required. In this embodiment, a system 134, according to further aspects of the invention, is shown treating an obstruction, more particularly, a kidney stone 131. The system includes a catheter 133 that terminates at its distal end with an electrode pair 132 similar to electrode pair 25 of FIGS. 1 and 2. The system further includes a power source 140. The power source has a positive output terminal 142 and a negative output terminal 144. The center electrode of the electrode pair 132 may be coupled to the positive terminal 142 of source 140 and the ring electrode of the electrode pair 132 may be coupled to the negative terminal 144 of the source 140. The electrodes of the electrode pair 132 may be formed of metal, such as stainless steel, and are maintained a controlled distance apart to allow a reproducible arc to form for a given applied voltage and current.

The catheter 133 of system 134 is shown in a ureter 130. The ureter has a kidney stone 131 requiring treatment. According to this embodiment, voltage pulses are applied to the electrode pair 132 to produce leading edge shock waves as previously described. The shock waves propagate through the fluid within the ureter and impinge directly on the kidney stone 131. In a manner as previously described, the power source may be operated to maintain the energy applied to the electrode pair within limits to assure that the steam bubbles produced by the generated arcs do not harm the ureter. To that end, the amplitude or pulse rate of the applied voltages may be controlled. Hence, by controlling the energy of the current during the produced arc, such as by controlling the on time of the current, barotrauma to the ureter may be minimized even though a balloon is not employed as in previous embodiments. Of course, the system of FIG. 9 may be used in other body organs as well, such as the bile duct, for example.

Figure 10:
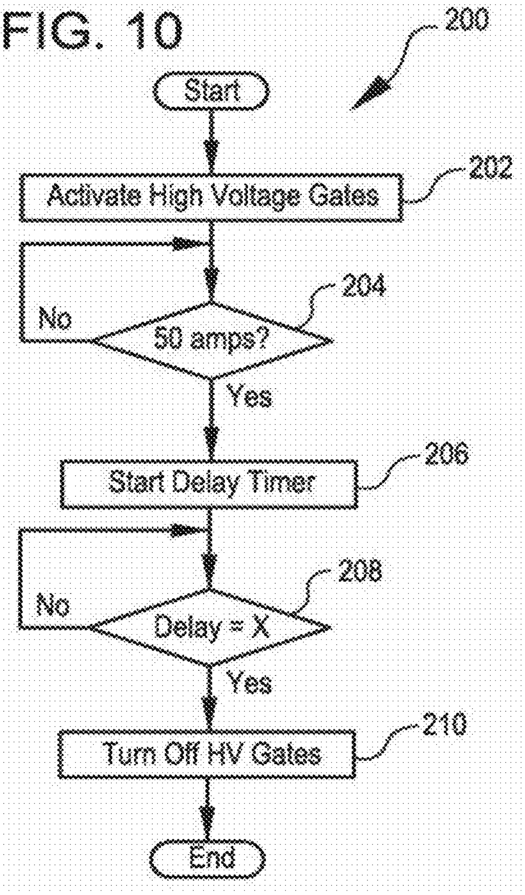
FIG. 10 is a flow diagram illustrating a further embodiment of the invention.

FIG. 10 is a flow diagram illustrating the process of a further embodiment of the invention. The embodiment of FIG. 10 takes into account the time it takes for a high voltage switch, such as switch 86 (FIG. 6), to turn off (the turn off time) and the rise time of the current flowing through the electrodes once the electrical arc starts. The current through the electrodes can eventually reach one-hundred amperes or more, at which point the maximum intensity shock wave will be formed. In order to permit the maximum current to be reached and to account for the turn off time of the switch 86, a delay is timed extending from when the current flowing through the electrodes is at a fixed threshold known to be below the maximum current, to the turn off time of the switch before the expected current maximum. For example, the current threshold may be fifty amperes. When the current through the electrodes equals fifty amperes, the delay timing is begun by the starting of a delay timer within the microprocessor 90. If the current is expected to be at a maximum 200 nanoseconds after the current reaches fifty amperes, and if it takes 100 nanoseconds for the high voltage switch to actually turn off after receiving a turn off signal, a delay of 100 nanoseconds should be timed from the 50 ampere sensing before a turn off signal is applied to the high voltage switch. Hence, a total time of 200 nanoseconds will pass after the current reaches 50 amperes and, as a result, will reach its maximum. As the current reaches its maximum, or shortly thereafter, the voltage applied to the electrodes will be terminated.

Referring now to the flow diagram 200 of FIG. 10, and also with reference to FIG. 6, the process begins with activity step 202 wherein the high voltage is applied to the output terminals 82 and 84 for application to the electrodes, for example, electrodes 22 and 24 (FIG. 1). At first, the current initially flowing through the electrodes is relatively low. However, after a dwell time, the applied high voltage causes an electrical arc to begin to form between the electrodes, the current through the electrodes is sensed, and the current rapidly rises. The current through the electrodes is sensed as previously described. At decision block 204, the microprocessor 90 determines if the sensed current has reached fifty amperes. When the current reaches fifty amperes, the process advances to activity block 206 where the timing of the aforementioned delay time (x) is started. Next, in decision block 208, it is determined when the delay time has been timed. In accordance with this embodiment, the delay time (x) may be 100 nanoseconds. When the delay time of 100 nanoseconds is timed, the process advances to activity block 210 wherein the process completes with a turn off signal being applied by the microprocessor 90 to the high voltage switch 86. The switch 86 will actually turn of a turn of time after the turn off signal is applied to the switch 86. Since it takes 100 nanoseconds for the switch to turn off and since 100 nanoseconds are timed before the turn off signal is applied to the switch, 200 nanoseconds form the 50 ampere current sensing will pass before the applied voltage to the electrodes is actually terminated. That provides sufficient time for the current to reach its maximum to generate the maximum intensity shock wave. The voltage application will terminated as the current reaches maximum, or shortly thereafter.

As a result of the foregoing, a maximum intensity shock wave is formed without wasting energy, without unduly eroding the electrodes, and without generating unnecessary heat. As may be appreciated, the delay timing may be employed to advantage in each of the embodiments disclosed herein including the embodiment of FIG. 9 which does not require a balloon.

While particular embodiments of the present invention have been shown and described, modifications may be made. It is therefore intended in the appended claims to cover all such changes and modifications which fall within the true spirit and scope of the invention as defined by those claims.

What is claimed is:

1. A catheter for delivering shockwaves to a calcified lesion comprising:

an elongated carrier;

a pair of electrodes carried by the elongated carrier, said pair of electrodes being immersed in a conductive fluid; and a power source with a circuit coupled to the pair of electrodes for supplying voltage pulses to the pair of electrodes, said power source including at least one capacitor and at least one solid state switch, each of the voltage pulses being generated by controlling the at least one solid state switch to cause a charge stored on the at least one capacitor to be delivered to the pair of electrodes, each voltage pulse having sufficient energy to generate an arc in the conductive fluid and allowing current to flow across the pair of electrodes to produce a shock wave, wherein the power source includes at least one sensor for monitoring at least one parameter of the circuit that varies in response to each voltage pulse, and wherein for a given voltage pulse the power source controls the at least one solid state switch to terminate the delivery of the voltage pulse across the pair of electrodes in response to the at least one parameter reaching at least one predetermined value, the at least one predetermined value being selected to ensure the creation of the arc for the voltage pulse, wherein the power source controls the at least one solid state switch to terminate the delivery of the voltage pulse in order to prevent a remaining charge on the at least one capacitor from being delivered to the pair of electrodes thereby conserving electrode material.

2. The catheter of claim 1, wherein the power source is configured to terminate the delivery of each of the voltage pulses across the pair of electrodes by activating a delay timer in response to the at least one parameter reaching the at least one predetermined value prior to the at least one solid state switch being opened.

3. The catheter of claim 2, wherein a duration of the delay timer is based on an estimated time from the at least one parameter reaching the at least one predetermined value to the at least one parameter reaching a maximum value.

4. The catheter of claim 2, wherein a duration of the delay timer is based on a predetermined time delay from when the at least one solid state switch receives a signal from the power source to terminate the delivery of the voltage pulse to when the delivery of the voltage pulse is terminated.

5. The catheter of claim 1, wherein the at least one sensor is a current sensor that includes a resistor, and wherein a voltage drop across the resistor is monitored to determine the current flowing between the pair of electrodes.

6. The catheter of claim 5, wherein the power source is configured to control the at least one solid state switch to terminate the delivery of each of the voltage pulses across the pair of electrodes in response to determining that the current flowing between the pair of electrodes has reached 50 amperes.

7. The catheter of claim 1, wherein the at least one predetermined value is selected to ensure creation of a steam bubble by the shock wave.

8. The catheter of claim 7, wherein the at least one predetermined value is selected to minimize energy available for a trailing shock wave associated with the subsequent collapse of the steam bubble.

9. The catheter of claim 1, wherein a dwell time between initial delivery of a given voltage pulse and creation of the arc is variable from pulse to pulse and the at least one predetermined value is high enough to ensure the creation of the arc while compensating for the dwell time.

10. The catheter of claim 1, wherein the at least one solid state switch is an insulated gate bipolar transistor (IGBT).

11. The catheter of claim 10, wherein the IGBT is driven by a FET driver.

12. The catheter of claim 11, wherein a gate of the IGBT is negatively biased by the FET driver to facilitate the opening of the IGBT.

13. The catheter of claim 1, wherein the catheter further comprises a temperature sensor communicatively coupled to the power source and configured to monitor a temperature of the conductive fluid.

14. The catheter of claim 13, wherein the temperature sensor is configured to cause the power source to control the at least one solid state switch to terminate the delivery of each of the voltage pulses across the pair of electrodes in response to determining that the temperature of the conductive fluid exceeds a predetermined temperature value.

15. The catheter of claim 13, wherein the predetermined temperature value is greater than or equal to about 2° C. above ambient body temperature.

16. The catheter of claim 13, wherein the temperature sensor is configured to cause the power source to control the at least one solid state switch to adjust a pulse rate of each of the voltage pulses across the pair of electrodes in response to determining that the temperature of the conductive fluid exceeds the predetermined temperature value.

17. The catheter of claim 1, wherein the elongated carrier is a hollow sheath, wherein the catheter further comprises a balloon attached to the hollow sheath, and wherein the balloon is filled with the conductive fluid.

18. The catheter of claim 1, wherein the conductive fluid comprises x-ray contrast.

19. The catheter of claim 1, wherein the calcified lesion is located within a vein or an artery.

* * * * *